(12) United States Patent
Barnett

(10) Patent No.: US 11,357,620 B1
(45) Date of Patent: Jun. 14, 2022

(54) EXCHANGEABLE OPTICS AND THERAPEUTICS

(71) Applicant: California LASIK & Eye, Inc., Sacramento, CA (US)

(72) Inventor: Bradley P. Barnett, Sacramento, CA (US)

(73) Assignee: CALIFORNIA LASIK & EYE, INC., Sacramento, CA (US)

( * ) Notice: Subject to any disclaimer, the term of this patent is extended or adjusted under 35 U.S.C. 154(b) by 0 days.

(21) Appl. No.: 17/471,496

(22) Filed: Sep. 10, 2021

(51) Int. Cl.
*A61F 2/16* (2006.01)
*A61L 27/54* (2006.01)

(52) U.S. Cl.
CPC .......... *A61F 2/1648* (2013.01); *A61F 2/1624* (2013.01); *A61F 2/1602* (2013.01); *A61F 2002/1682* (2015.04); *A61F 2002/16902* (2015.04); *A61L 27/54* (2013.01)

(58) Field of Classification Search
CPC .................. A61F 2/1602; A61F 2/1648; A61F 2002/16902; A61L 27/54
See application file for complete search history.

(56) References Cited

U.S. PATENT DOCUMENTS

| | | | |
|---|---|---|---|
| 3,937,222 A | 2/1976 | Banko | |
| 4,168,547 A | 9/1979 | Konstantinov et al. | |
| 4,298,996 A | * 11/1981 | Barnet | A61F 2/16 623/6.43 |
| 4,409,691 A | 10/1983 | Levy | |
| 4,435,856 A | 3/1984 | L'Esperance | |
| 4,494,254 A | 1/1985 | Lopez | |
| 4,681,102 A | 7/1987 | Bartell | |
| 4,693,245 A | 9/1987 | Pao | |
| 4,741,330 A | 5/1988 | Hayhurst | |
| 4,769,035 A | 9/1988 | Kelman | |
| 4,816,031 A | 3/1989 | Pfoff | |
| 4,828,558 A | 5/1989 | Kelman | |
| 4,842,601 A | 6/1989 | Smith | |
| 4,878,910 A | 11/1989 | Koziol et al. | |
| 4,932,971 A | 6/1990 | Kelman | |
| 4,950,272 A | 8/1990 | Smirmaul | |
| 4,950,289 A | 8/1990 | Krasner | |
| 4,960,418 A | 10/1990 | Tennant | |

(Continued)

FOREIGN PATENT DOCUMENTS

| | | |
|---|---|---|
| AU | 2018271403 B2 | 2/2019 |
| AU | 2017345731 B2 | 10/2019 |

(Continued)

*Primary Examiner* — Javier G Blanco
(74) *Attorney, Agent, or Firm* — Talem IP Law, LLP

(57) ABSTRACT

An exchangeable optics system includes an intraocular base that can be fixed within an eye. The intraocular base includes one or more couplers and a supporting structure. The one or more couplers releasably couple to an exchangeable optic or therapeutic and can include magnetic material. The supporting structure can include haptics and a main structure that physically supports the exchangeable optic or the therapeutic that is coupled via the one or more couplers. In some cases, the intraocular base can include a fixed lens within or on the main structure. The exchangeable optic can include corresponding one or more couplers, which may be formed of magnetic material. The therapeutic can be in the form of a magnetic particle.

6 Claims, 15 Drawing Sheets

(56) References Cited

U.S. PATENT DOCUMENTS

| | | |
|---|---|---|
| 5,026,396 A | 6/1991 | Darin |
| 5,098,444 A | 3/1992 | Feaster |
| 5,123,905 A | 6/1992 | Kelman |
| 5,133,747 A | 7/1992 | Feaster |
| 5,147,369 A | 9/1992 | Wagner |
| 5,152,788 A | 10/1992 | Isaacson et al. |
| 5,201,762 A | 4/1993 | Hauber |
| 5,222,981 A | 6/1993 | Werblin |
| 5,304,182 A | 4/1994 | Rheinish et al. |
| 5,323,788 A | 6/1994 | Silvestrini et al. |
| 5,354,335 A | 10/1994 | Lipshitz et al. |
| 5,358,520 A | 10/1994 | Patel |
| 5,378,475 A | 1/1995 | Smith et al. |
| 5,410,375 A | 4/1995 | Fiala |
| 5,417,369 A | 5/1995 | Lipson |
| 5,507,805 A | 4/1996 | Koeniger |
| 5,578,081 A | 11/1996 | McDonald |
| 5,616,120 A | 4/1997 | Andrew et al. |
| 5,628,795 A | 5/1997 | Langerman |
| 5,728,155 A | 3/1998 | Anello et al. |
| 5,769,890 A | 6/1998 | McDonald |
| 5,814,103 A | 9/1998 | Lipshitz et al. |
| 5,824,074 A | 10/1998 | Koch |
| 5,860,985 A | 1/1999 | Anschutz |
| 5,876,442 A | 3/1999 | Lipshitz et al. |
| 5,895,422 A | 4/1999 | Hauber |
| 5,902,598 A | 5/1999 | Chen et al. |
| 5,928,283 A | 7/1999 | Gross et al. |
| 5,944,725 A | 8/1999 | Cicenas et al. |
| 5,968,094 A | 10/1999 | Werblin et al. |
| 6,027,531 A | 2/2000 | Tassignon |
| 6,066,171 A | 5/2000 | Lipshitz et al. |
| 6,090,141 A | 7/2000 | Lindstrom |
| 6,113,633 A | 9/2000 | Portney |
| 6,197,057 B1 | 3/2001 | Peyman et al. |
| 6,197,058 B1 | 3/2001 | Portney |
| 6,228,113 B1 | 5/2001 | Kaufman |
| 6,231,603 B1 | 5/2001 | Lang et al. |
| 6,261,321 B1 | 7/2001 | Kellan |
| 6,277,146 B1 | 8/2001 | Peyman et al. |
| 6,280,471 B1 | 8/2001 | Peyman et al. |
| 6,358,280 B1 | 3/2002 | Herrick |
| 6,413,276 B1 | 7/2002 | Werblin |
| 6,423,094 B1 | 7/2002 | Sarfarazi |
| 6,461,384 B1 | 10/2002 | Hoffmann et al. |
| 6,464,725 B2 | 10/2002 | Skotton |
| 6,488,708 B2 | 12/2002 | Sarfarazi |
| 6,537,281 B1 | 3/2003 | Portney |
| 6,551,354 B1 | 4/2003 | Ghazizadeh et al. |
| 6,554,859 B1 | 4/2003 | Lang et al. |
| 6,558,420 B2 | 5/2003 | Green |
| 6,596,026 B1 | 7/2003 | Gross et al. |
| 6,599,317 B1 | 7/2003 | Weinschenk, III et al. |
| 6,616,691 B1 | 9/2003 | Tran |
| 6,616,692 B1 | 9/2003 | Glick et al. |
| 6,638,304 B2 | 10/2003 | Azar |
| 6,695,881 B2 | 2/2004 | Peng et al. |
| 6,764,511 B2 | 7/2004 | Zadno-Azizi et al. |
| 6,767,363 B1 | 7/2004 | Bandhauer et al. |
| 6,797,004 B1 | 9/2004 | Brady et al. |
| 6,818,017 B1 | 11/2004 | Shu |
| 6,849,091 B1 | 2/2005 | Cumming |
| 6,960,231 B2 | 11/2005 | Tran |
| 6,972,032 B2 | 12/2005 | Aharoni et al. |
| 6,991,651 B2 | 1/2006 | Portney |
| 7,008,447 B2 | 3/2006 | Koziol |
| 7,018,409 B2 | 3/2006 | Glick et al. |
| 7,081,134 B2 | 7/2006 | Cukrowski |
| 7,097,660 B2 | 8/2006 | Portney |
| 7,101,397 B2 | 9/2006 | Aharoni |
| 7,122,053 B2 | 10/2006 | Esch |
| 7,125,422 B2 | 10/2006 | Woods et al. |
| 7,150,760 B2 | 12/2006 | Zhang |
| 7,186,266 B2 | 3/2007 | Peyman |
| 7,198,640 B2 | 4/2007 | Nguyen |
| 7,220,278 B2 | 5/2007 | Peyman |
| 7,223,288 B2 | 5/2007 | Zhang et al. |
| 7,238,201 B2 | 7/2007 | Portney et al. |
| 7,300,464 B2 | 11/2007 | Tran |
| 7,316,713 B2 | 1/2008 | Zhang |
| 7,455,691 B2 | 11/2008 | Feingold et al. |
| 7,582,113 B2 | 9/2009 | Terwee |
| 7,591,849 B2 | 9/2009 | Richardson |
| 7,645,299 B2 | 1/2010 | Koziol |
| 7,662,179 B2 | 2/2010 | Sarfarazi |
| 7,727,277 B2 | 6/2010 | Aharoni et al. |
| 7,780,729 B2 | 8/2010 | Nguyen et al. |
| 7,857,850 B2 | 12/2010 | Mentak et al. |
| 7,871,437 B2 | 1/2011 | Hermans et al. |
| 7,918,886 B2 | 4/2011 | Aharoni et al. |
| 7,985,253 B2 | 7/2011 | Cumming |
| 7,993,399 B2 | 8/2011 | Peyman |
| 7,998,198 B2 | 8/2011 | Angelopoulos et al. |
| 8,012,204 B2 | 9/2011 | Weinschenk, III et al. |
| 8,034,106 B2 | 10/2011 | Mentak et al. |
| 8,034,107 B2 | 10/2011 | Stenger |
| 8,034,108 B2 | 10/2011 | Bumbalough |
| 8,062,361 B2 | 11/2011 | Nguyen et al. |
| 8,066,768 B2 | 11/2011 | Werblin |
| 8,137,399 B2 | 3/2012 | Glazier et al. |
| 8,167,941 B2 | 5/2012 | Boyd et al. |
| 8,187,325 B2 | 5/2012 | Zadno-Azizi et al. |
| 8,197,541 B2 | 6/2012 | Schedler |
| 8,273,123 B2 | 9/2012 | Ben Nun |
| 8,287,593 B2 | 10/2012 | Portney |
| 8,377,124 B2 | 2/2013 | Hong et al. |
| 8,377,125 B2 | 2/2013 | Kellan |
| 8,480,734 B2 | 7/2013 | Kellan et al. |
| 8,728,158 B2 | 5/2014 | Whitsett |
| 8,758,434 B2 | 6/2014 | Scott |
| 8,900,300 B1 | 12/2014 | Wortz |
| 9,078,744 B2 | 7/2015 | Van Noy |
| 9,339,375 B2 | 5/2016 | Lee et al. |
| 9,358,103 B1 | 6/2016 | Wortz et al. |
| 9,364,316 B1 | 6/2016 | Kahook et al. |
| 9,414,907 B2 | 8/2016 | Wortz et al. |
| 9,486,311 B2 | 11/2016 | Argento et al. |
| 9,681,946 B2 | 6/2017 | Kahook et al. |
| 9,757,227 B2 | 9/2017 | Kushlin et al. |
| 9,763,776 B2 | 9/2017 | Lee |
| 10,028,824 B2 | 7/2018 | Kahook et al. |
| 10,052,196 B2 | 8/2018 | Pugh et al. |
| 10,080,648 B2 | 9/2018 | Kahook et al. |
| 10,195,018 B2 | 2/2019 | Salahieh et al. |
| 10,350,056 B2 | 7/2019 | Argento et al. |
| 10,444,541 B2 | 10/2019 | Hyde et al. |
| 10,485,654 B2 | 11/2019 | Brady et al. |
| 10,526,353 B2 | 1/2020 | Silvestrini |
| 10,548,718 B2 | 2/2020 | Salahieh et al. |
| 10,647,831 B2 | 5/2020 | Silvestrini et al. |
| 10,772,721 B2 | 9/2020 | Rao et al. |
| 10,799,340 B2 | 10/2020 | Collins et al. |
| 10,820,985 B2 | 11/2020 | Wortz |
| 10,842,615 B2 | 11/2020 | Wortz et al. |
| 10,842,616 B2 | 11/2020 | Silvestrini et al. |
| 10,856,969 B2 | 12/2020 | Ishikawa |
| 11,076,948 B2 | 8/2021 | Kahook et al. |
| 2002/0128710 A1* | 9/2002 | Eggleston ............ A61F 2/1613 623/6.22 |
| 2003/0088253 A1 | 5/2003 | Seil |
| 2003/0144733 A1 | 7/2003 | Brady et al. |
| 2003/0158560 A1 | 8/2003 | Portney |
| 2004/0010310 A1 | 1/2004 | Peyman |
| 2004/0106993 A1 | 6/2004 | Portney |
| 2004/0117011 A1* | 6/2004 | Aharoni ............ A61N 1/36046 623/4.1 |
| 2004/0148022 A1 | 7/2004 | Eggleston |
| 2004/0236422 A1 | 11/2004 | Zhang et al. |
| 2004/0243142 A1 | 12/2004 | Siepser |
| 2005/0015144 A1 | 1/2005 | Tran |
| 2005/0027354 A1 | 2/2005 | Brady et al. |
| 2005/0125058 A1 | 6/2005 | Cumming et al. |
| 2005/0131535 A1 | 6/2005 | Woods |
| 2005/0187621 A1 | 8/2005 | Brady |

(56) References Cited

U.S. PATENT DOCUMENTS

| | | |
|---|---|---|
| 2006/0111776 A1 | 5/2006 | Glick et al. |
| 2006/0286147 A1 | 12/2006 | Salamone et al. |
| 2007/0123981 A1 | 5/2007 | Tassignon |
| 2007/0129801 A1 | 6/2007 | Cumming |
| 2007/0260308 A1 | 11/2007 | Tran |
| 2008/0046077 A1 | 2/2008 | Cumming |
| 2008/0103592 A1 | 5/2008 | Maloney |
| 2009/0005864 A1 | 1/2009 | Eggleston |
| 2009/0125106 A1 | 5/2009 | Weinschenk, III et al. |
| 2010/0016964 A1 | 1/2010 | Werblin |
| 2010/0047355 A1* | 2/2010 | Bulte ............... A61K 49/0002 424/490 |
| 2010/0204787 A1 | 8/2010 | Van Noy |
| 2010/0298933 A1 | 11/2010 | Knox et al. |
| 2011/0040378 A1 | 2/2011 | Werblin |
| 2011/0054600 A1 | 3/2011 | Bumbalough |
| 2011/0104052 A1* | 5/2011 | Barnett ............... A61K 9/1635 424/1.25 |
| 2011/0251686 A1 | 10/2011 | Masket |
| 2011/0307058 A1 | 12/2011 | Beer |
| 2011/0313521 A1 | 12/2011 | Angelopoulos |
| 2012/0078364 A1 | 3/2012 | Stenger |
| 2012/0179249 A1 | 7/2012 | Coleman |
| 2013/0184815 A1 | 7/2013 | Roholt |
| 2013/0190868 A1 | 7/2013 | Kahook et al. |
| 2013/0296694 A1 | 11/2013 | Ehlers et al. |
| 2014/0081178 A1 | 3/2014 | Pletcher et al. |
| 2014/0085599 A1 | 3/2014 | Etzkorn |
| 2014/0085600 A1 | 3/2014 | Pletcher et al. |
| 2014/0085602 A1 | 3/2014 | Ho et al. |
| 2014/0087452 A1 | 3/2014 | Liu et al. |
| 2014/0088381 A1 | 3/2014 | Etzkorn et al. |
| 2014/0098226 A1 | 4/2014 | Pletcher et al. |
| 2014/0107777 A1 | 4/2014 | Portney |
| 2014/0180411 A1 | 6/2014 | Tornambe et al. |
| 2014/0192311 A1 | 7/2014 | Pletcher et al. |
| 2014/0194710 A1 | 7/2014 | Ho et al. |
| 2014/0194713 A1 | 7/2014 | Liu |
| 2014/0194773 A1 | 7/2014 | Pletcher et al. |
| 2014/0371852 A1 | 12/2014 | Aharoni et al. |
| 2015/0230981 A1 | 8/2015 | Kahook et al. |
| 2015/0366660 A1* | 12/2015 | Fernández Martínez .................... A61F 2/16015 623/6.22 |
| 2016/0074154 A1 | 3/2016 | Woods |
| 2016/0235524 A1 | 8/2016 | Wortz et al. |
| 2016/0361156 A1 | 12/2016 | Brown |
| 2017/0319332 A1 | 11/2017 | Kahook et al. |
| 2017/0348095 A1 | 12/2017 | Wortz et al. |
| 2018/0161153 A1 | 6/2018 | Kahook et al. |
| 2018/0263761 A1* | 9/2018 | Bozukova ............ A61F 2/1654 |
| 2018/0368974 A1* | 12/2018 | Kahook ............... A61F 2/1662 |
| 2019/0021848 A1 | 1/2019 | Kahook et al. |
| 2019/0321219 A1 | 10/2019 | Ostermeier et al. |
| 2020/0022840 A1* | 1/2020 | Kahook ............... A61F 2/1613 |
| 2021/0161655 A1 | 6/2021 | Kaschke et al. |

FOREIGN PATENT DOCUMENTS

| | | |
|---|---|---|
| CA | 2350795 C | 7/2006 |
| CA | 2407432 C | 1/2007 |
| CA | 2480772 C | 11/2008 |
| CA | 2959354 C | 8/2018 |
| CA | 3095098 A1 | 10/2019 |
| CN | 104936553 B | 3/2017 |
| CN | 107205812 B | 11/2019 |
| CN | 107961101 B | 12/2019 |
| DE | 102016221371 A1 | 5/2018 |
| DE | 102017112085 A1 | 12/2018 |
| EP | 1138282 A1 | 10/2001 |
| EP | 1202684 B1 | 4/2003 |
| EP | 1457170 A1 | 9/2004 |
| EP | 1200019 B1 | 9/2005 |
| EP | 2042124 A1 | 4/2009 |
| EP | 1278483 B1 | 8/2011 |
| ES | 2233049 T3 | 6/2005 |
| ES | 2300278 T3 | 6/2008 |
| ES | 2379781 T3 | 5/2012 |
| JP | S6222641 A | 1/1987 |
| JP | S6389154 A | 4/1988 |
| JP | H06165793 A | 6/1994 |
| JP | 2003524503 A | 8/2003 |
| JP | 4261488 B2 | 4/2009 |
| JP | 4486122 B2 | 6/2010 |
| JP | 4511533 B2 | 7/2010 |
| JP | 2012040326 A | 3/2012 |
| JP | 5379152 B2 | 12/2013 |
| JP | 5705529 B2 | 4/2015 |
| JP | 6030089 B2 | 11/2016 |
| JP | 6270739 B2 | 1/2018 |
| JP | 6499307 B2 | 4/2019 |
| JP | 2019520886 A | 7/2019 |
| JP | 6779262 B2 | 11/2020 |
| KR | 100913267 B1 | 8/2009 |
| WO | 94/28825 A1 | 12/1994 |
| WO | 2005084587 A3 | 9/2005 |
| WO | 2006050171 A2 | 5/2006 |
| WO | 2008094518 A1 | 8/2008 |
| WO | 2009073193 A2 | 6/2009 |
| WO | 2010002215 A2 | 1/2010 |
| WO | 2012023133 A1 | 2/2012 |
| WO | 2013112589 A1 | 8/2013 |
| WO | 2013158942 A1 | 10/2013 |
| WO | 2014197170 A1 | 12/2014 |
| WO | 2014204575 A1 | 12/2014 |
| WO | 2015195825 A1 | 12/2015 |
| WO | 2016022995 A2 | 2/2016 |
| WO | 2016126285 A1 | 8/2016 |

* cited by examiner

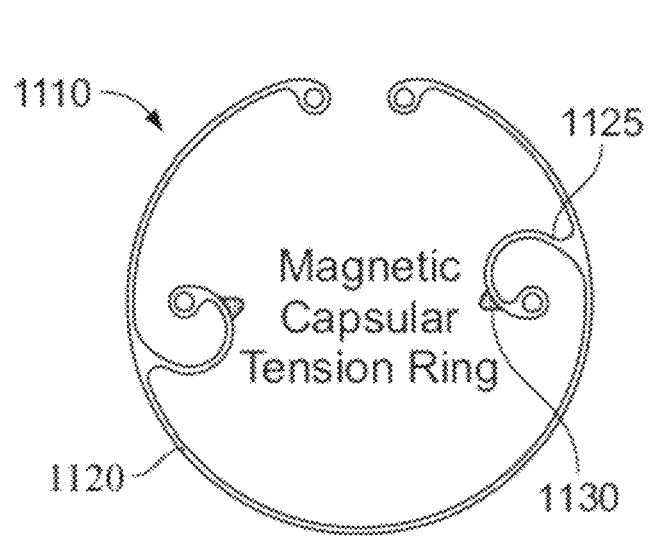 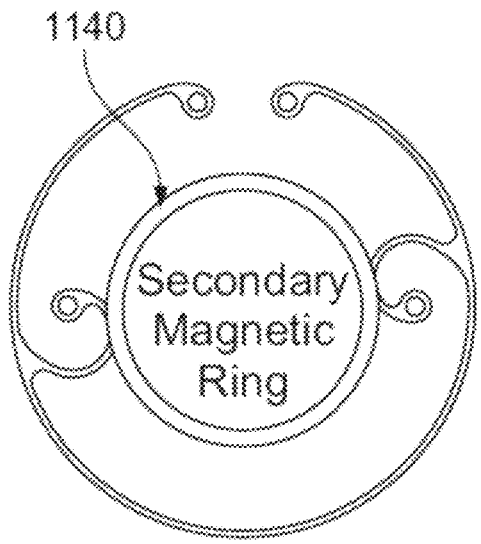
Figure 11A  Figure 11B
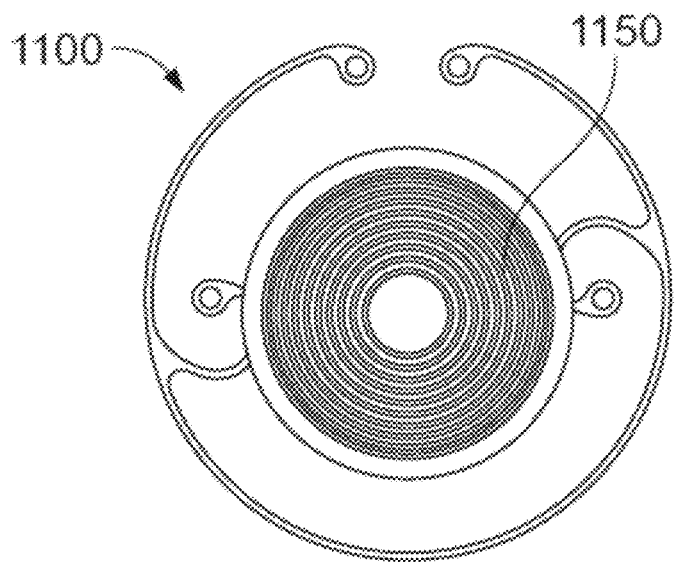
Figure 11C
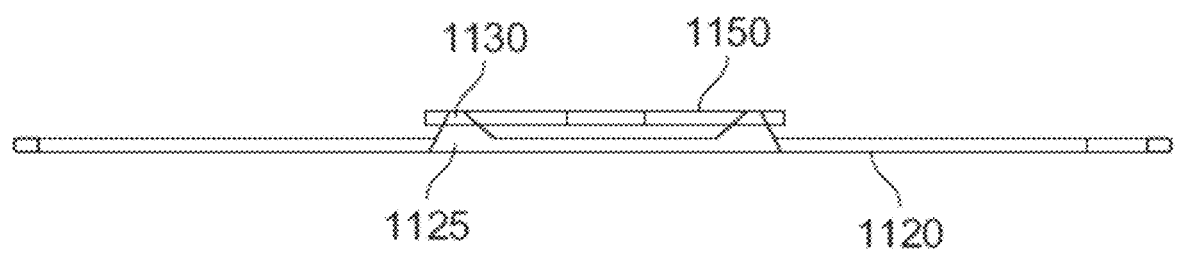
Figure 11D

EXCHANGEABLE OPTICS AND THERAPEUTICS

BACKGROUND

An intraocular lens (IOL) is a lens that is implanted in the eye. IOLs come in phakic, designed to be implanted without performing cataract surgery, and pseudophakic, designed to be implanted in conjunction with cataract surgery, varieties. A phakic IOL has the ability to reside in the sulcus space between the capsular bag and the iris or alternatively can reside in the anterior chamber, between the iris and cornea. The most commonly employed pseudophakic IOL is posterior chamber IOL includes haptics that enable the lens to be held in place in the capsular bag inside the eye. Implantation of an IOL is often carried out by an eye surgeon in a surgical center, but may be also be performed at an ophthalmologist's office in an in office surgical suite. In office procedures are particularly common with phakic IOLs, much in the same way laser refractive surgeries are typically in office. The field of pseudophakic IOLs is increasingly addressing the issue of presbyopia, which is the case where someone is not able to see both at distance and near. Presbyopia is not an indication for insurance coverage of cataract surgery currently.

As the field matures, it is likely IOLs will be increasingly utilized to address presbyopia, instead of glare and blurred vision even with glasses or some form of wearable refractive correction which is the current indication. To achieve the quality of vision of laser refractive surgery and to enable incremental changes to the lens as the technology improves, a means of fully customizable and upgradeable IOL design is sorely needed. Refractive cataract surgery replaces the natural eye lens with an advanced multi-focal or extended-depth-of-focus (EDOF) IOL. Refractive cataract surgery has not achieved the precision of corneal refractive surgery, such as LASIK (laser-assisted in situ keratomileusis), which can be individualized to high precision. Moreover, there currently is a lack of wave-front guided precision in cataract extraction and IOL implantation.

A wavefront-guided approach refers to an ablation profile that considers preoperative higher-order aberrations, where the final goal is to avoid inducing aberrations and to eliminate some that exist. This is commonly employed with laser refractive surgery such as LASIK and PRK, as all variables in the eye are known. The laser ablation profile is computed preoperatively according to the results of aberrometry and is transferred to a laser system for use, for example, during surgery. The only modification made to the eye is to the shape of the cornea. Currently this is an elusive task in cataract surgery for two reasons. Principally, the effective lens position, where the IOL ends up in the eye, is hard to determine. Small changes in the anterior posterior position make large changes in the total power of the lens. In addition, zonular weakness induced by the surgery and change in corneal astigmatism made by the cataract main incision can respectively change the lens position and the corneal curvature. Moreover, any customized, astigmatism and higher order aberration correction is precluded a priori on the IOL is precluded by potential shifting of the IOL within the capsular bag in the X, Y, Z plane.

Outside of the inability to provide wavefront guided IOL optimization, current IOL systems do not enable ease of correction if a non-optimal IOL is placed, nor do they allow for ease of upgradeability. IOL exchange is a challenging procedure that even in the most skilled surgeon's hands results in significant trauma to the ocular structures. So much so that IOL exchange is viewed as a last resort. However, repeated removal and replacement of a conventional IOL may not be an easy procedure and can result in complications. For example, IOL exchange with the conventional IOLs requires dissection of the capsular bag and retrieval of an unfolded lens through the cornea or sclera. Either retrieval approach (through the cornea or through the sclera) is highly traumatic to the eye and its delicate structures. Instead of exchanging IOLs, most surgeons will perform LASIK or other laser refractive procedure to the cornea. This also is not infinitely repeatable as corneal tissue is ablated at each procedure. Repeated laser correction can lead to a host of complications including corneal ectasia and epithelial ingrowth. It also can induce ocular surface disease in even young patients and thus is less than ideal in many of the older individuals undergoing cataract surgery.

A need exists for a system that enables relatively unlimited exchangeable optics as well as wavefront guided lens optimization.

BRIEF SUMMARY

Exchangeable optics and therapeutics are described that can enable progressive application and exchanges of lenses and/or therapeutics in the eye.

An exchangeable optics system includes an intraocular base that can be fixed within an eye. The intraocular base includes one or more couplers and a supporting structure. The one or more couplers can include magnetic material or other releasable fixation material or structures. For example, the releasable couplers can be in the form of a hook and loop coupler, a memory material fixation element such as what is utilized for tagging guns for affixing tags to clothing, a button fastener, a screw-type fastener, a hinge-based fastener similar to a cuff link, a suction cup based mechanism, an adhesive, or any other means of reversible fixation.

Magnetic fixation is particularly attractive as the base element to which the secondary optic couples can be in the capsular bag and the magnetic secondary optic can couple through magnetic force through the anterior capsular bag without physically directly contacting the IOL in the bag. Magnetic attraction is also an ideal mechanism as it allows for a secondary optic to be disengaged from the primary optic with minimal force. Accordingly for magnetic and other types of releasable couplers, it can be important to consider damage to delicate zonules that hold the capsular bag. The supporting structure can include haptics and a main structure that physically supports an exchangeable optic or therapeutic that is coupled via the one or more couplers. In some cases, the intraocular base can include a fixed lens within or on the main structure.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 7A shows another example of an intraocular base; and FIG. 7B shows application of a second optic onto the intraocular base and first optic using a delivery system.

FIGS. 11A-11D illustrate another example of an exchangeable optics system with magnetic exchangeable ocular lens.

DETAILED DESCRIPTION

Exchangeable optics and therapeutics are described that can enable progressive application and exchanges of lenses and/or therapeutics in the eye.

Figure 1A:
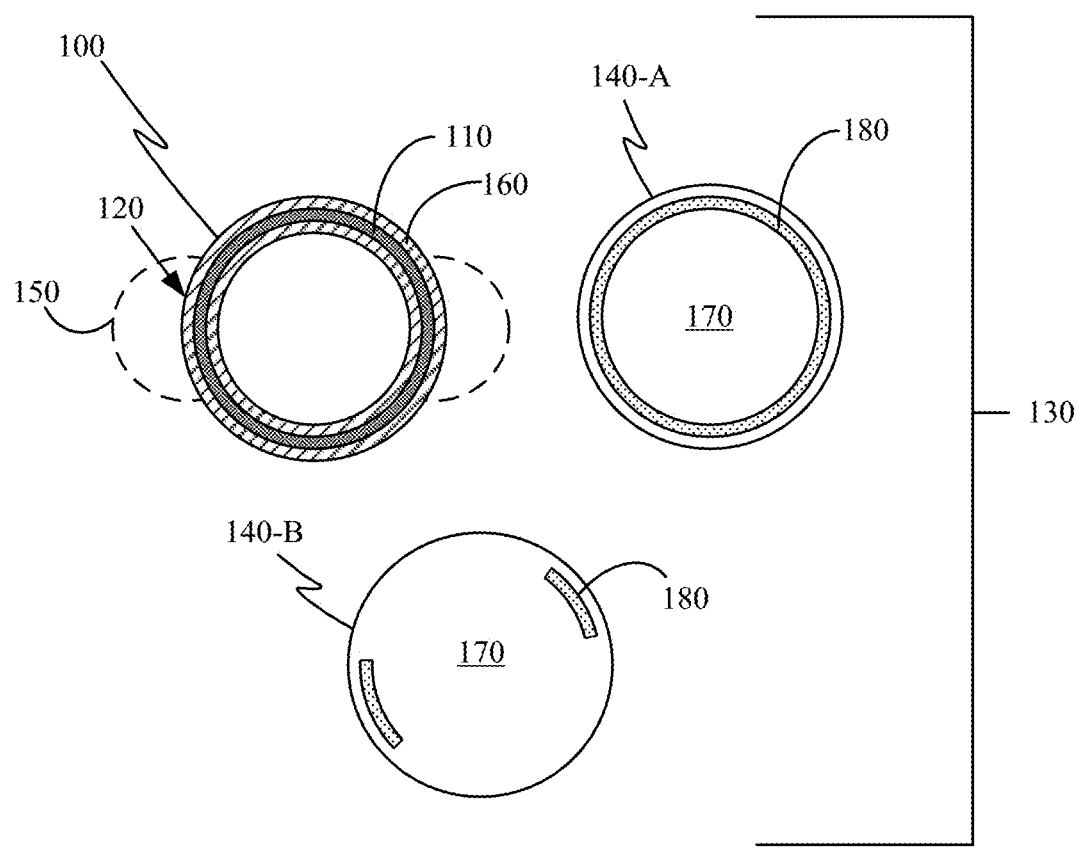
FIGS. 1A and 1B illustrate exchangeable optics systems suitable for an implantable intraocular lens and application of therapeutics.
Figure 1B:
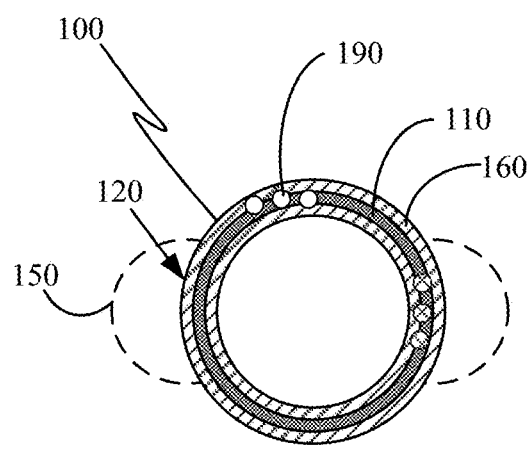

FIGS. 1A and 1B illustrate exchangeable optics systems suitable for an implantable intraocular lens and application of therapeutics. As shown in FIGS. 1A and 1B, Exchangeable optics systems include an intraocular base 100 that can be fixed within an eye. The intraocular base 100 includes one or more couplers (e.g., coupler 110) and a supporting structure 120. The one or more couplers can include magnetic material or other releasable fixation material or structures. In this example, a single ring-shaped coupler 110 is shown.

Referring to FIG. 1A, an exchangeable optics system 130 can include an intraocular base 100 that supports an exchangeable optic (e.g., 140-A, 140-B) and can be fixed within the eye. As mentioned above, the intraocular base 100 can include one or more couplers (e.g., coupler 110) and a supporting structure 120. The one or more couplers, in this case, ring-shaped coupler 110, are used to releasably couple the intraocular base 100 to the exchangeable optic 140-A, 140-B. The supporting structure 120 can include haptics 150 for suturing or otherwise fixing the intraocular base 100 in the eye and a main structure 160 (which may be a circular substructure), which can be used to physically support an exchangeable optic 140-A, 140-B directly or indirectly via the one or more couplers.

The haptics 150 can be any suitable structure enabling the intraocular base 100 to be fixed within the eye. Various examples are shown in FIGS. 6A, 7A, 10, 11A, and 12A-12D.

In the illustrated scenario, the main structure 160 is open in the center such that the exchangeable optic 140-A, 140-B rests on a proximal surface at the perimeter of the intraocular base 100. In other implementations, the main structure 160 has a transparent surface over which the exchangeable optic 140-A, 140-B rests. The supporting structure 120 can also optionally include a lens or IOL (not shown) within or on the main structure 160. In some cases, the supporting structure 120 can include one or more protrusions that can be used to extend up through a hole in the capsular bag of the eye (see e.g., extensions 222 of FIG. 2B and tension ring extensions 1125 of FIG. 11A). In some of such cases, a coupler can be disposed at an end of a protrusion. This coupler may be the coupler for the base or an additional coupler for the base.

Figure 9B:
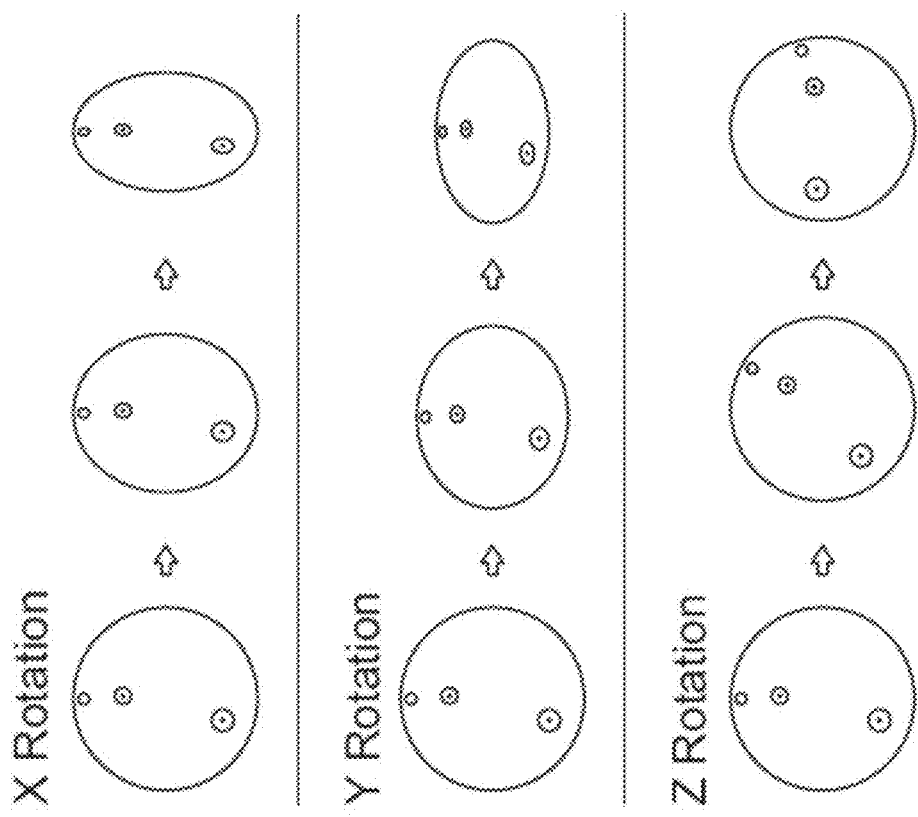
FIGS. 9A and 9B show fiducial designs that can enable precise orientation of three-dimensional rotation of an optic or haptic.
Figure 9A:
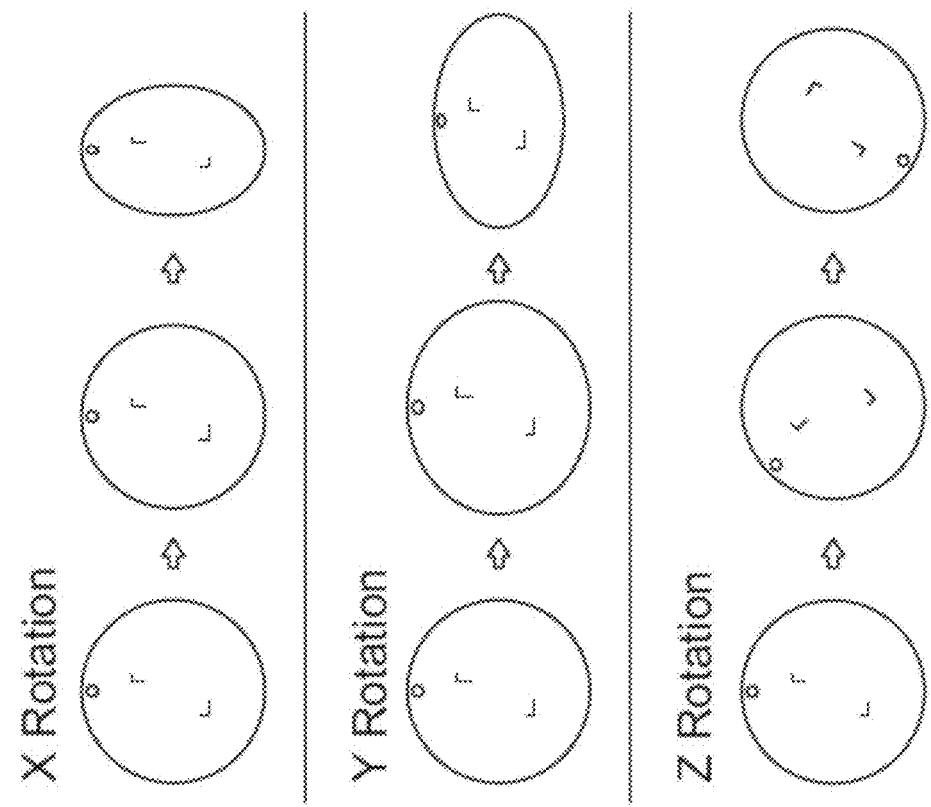

The exchangeable optic 140-A, 140-B can include a lens 170 and one or more corresponding couplers 180. For application of the exchangeable optics system 130, the intraocular base 100 can be deployed in an eye. One of the exchangeable optics 140-A, 140-B can then be deployed, oriented/aligned, and coupled to the intraocular base 100 using the couplers 110, 180 (illustrated as magnets/magnetic material). Alignment can involve radial alignment with respect to either the intraocular base, the eye, or some structure within the eye. The one or more exchangeable optics (e.g., optic 140-A, 140-B) can include fiducials to aid in radial alignment, such as seen in FIGS. 9A and 9B. Alignment can also involve depth alignment with respect to either the intraocular base, the eye, or some structure within the eye.

In some cases, there are more or fewer "corresponding couplers" 180 than there are couplers 110 of the intraocular base 100. For example, the couplers of the base may be point couplers while the couplers of the optic may be a single ring shape. In the illustrated scenario, one exchangeable optic 140-A is shown with a single corresponding coupler 180, which is in the shape of a ring; and the other exchangeable optic 140-B is shown with two corresponding couplers 180 that are positioned to both couple to the ring-shaped coupler 110 of the intraocular base 100. The coupling between the intraocular base 100 and the exchangeable optic 140-A, 140-B can be accomplished in a variety of ways, for example, magnetically, using friction, or chemically. In the illustrated scenario, magnetic coupling is shown.

Of course, while a ring-shape coupler 110 is one example, the one or more couplers at the intraocular base may be two couplers formed of magnetic material such that the coupling is accomplished using a two-point coupling where a first of the one or more couplers of the intraocular base is disposed at a proximal surface (i.e., the surface facing outward from the eye) on one side of the intraocular base and a second of the one or more couplers is disposed at the proximal surface on another side of the intraocular base. The corresponding one or more couplers would then be disposed at the exchangeable optic in a manner to orient and couple the exchangeable optic to the base. For example, the corresponding one or more couplers would be disposed in alignment for coupling to the one or more couplers of the intraocular base.

As mentioned above, the one or more couplers 110 and the corresponding one or more couplers 180 can be formed of magnetic material. The magnetic material can be any suitable ferromagnetic or ferrimagnetic material. The magnetic material is sized and shaped so as to minimize or avoid susceptibility to strong external magnetic fields such as MM (e.g., avoiding/minimizing movement or interference with imaging).

It should be understood that although the examples contained herein make reference to the couplers being magnets or magnetic, other types of releasable couplers can be used (e.g., chemical, mechanical, or friction based) in certain implementations. The use of magnetic couplers also enable certain therapeutics to be applied.

Indeed, referring to FIG. 1B, the same intraocular base 100 can be used to apply therapeutics 190. In the illustrated scenario, therapeutics 190 can be coupled to the intraocular base 100. In some cases, the therapeutics 190 are applied once the intraocular base 100 is deployed in the eye. In some cases, the therapeutics 190 may be applied before original deployment and then optionally reapplied after deployment.

Figure 2A:
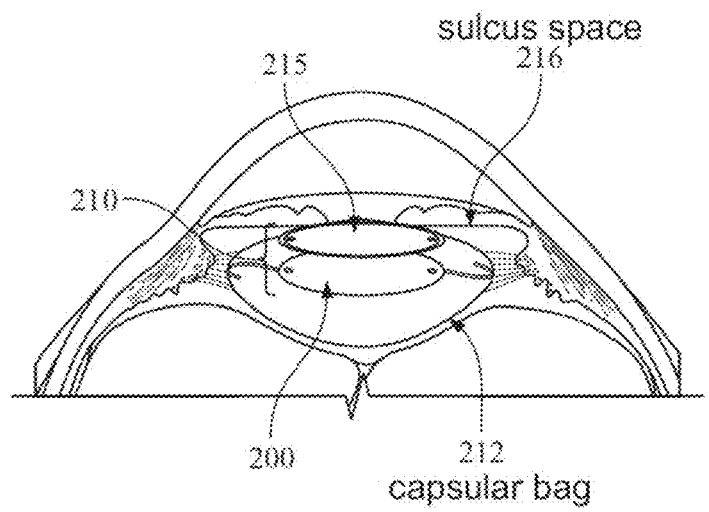
FIGS. 2A-2E illustrate various locations in the eye where an exchangeable optics system can be set.
Figure 2B:
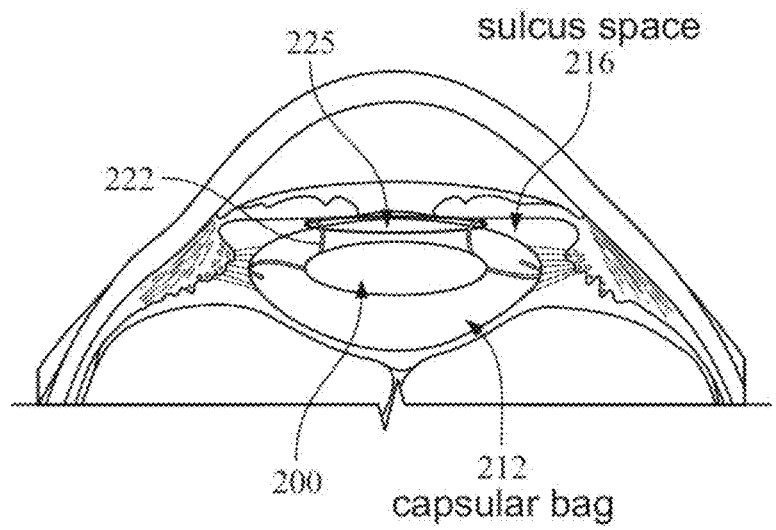
Figure 2C:
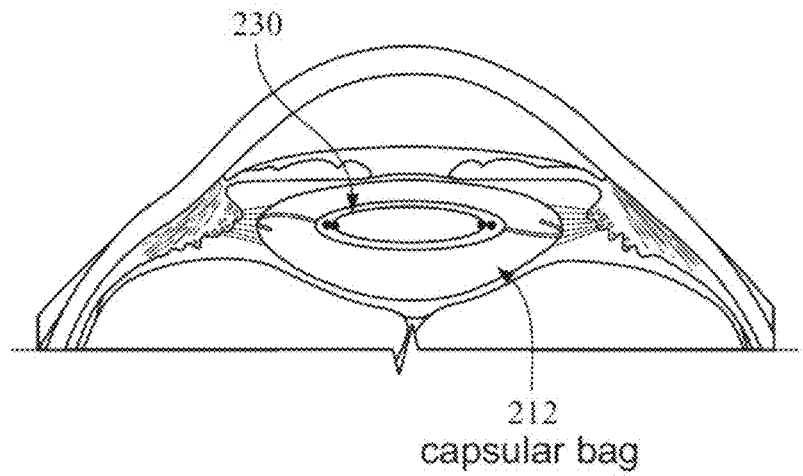

FIGS. 2A-2E illustrate various locations in the eye where an exchangeable optics system can be set. FIGS. 2A-2C show examples of an intraocular base of an exchangeable optics system being positioned within a capsular bag of the eye. Referring to FIG. 2A, an intraocular base 200 of an exchangeable optics system 210 can be positioned within the capsular bag 212 of an eye. Through use of magnetic coupling, an exchangeable optic 215 (or therapeutic) can be deployed to (and even later removed from) the sulcus space 216 of the eye. Referring to FIG. 2B, an intraocular base 220 having extensions 222 can be positioned within the capsular bag 212 of an eye. The extensions 222 (or other protruding structure) can be extended into the sulcus space 216 through one or more holes in the capsular bag 212. For example, there may be an opening from cataract surgery through which the extensions 222 can protrude. In some cases, small openings may be made to allow for the extensions 222 to protrude through. Magnetic, mechanical, or chemical couplers may be provided at the end of the extensions 222 for an exchangeable optic 225 that is deployed to (and even later removed from) the sulcus space 216 to couple to. Referring to FIG. 2C, an exchangeable optics system 230 can be positioned entirely within the capsular bag 212.

Figure 2D:
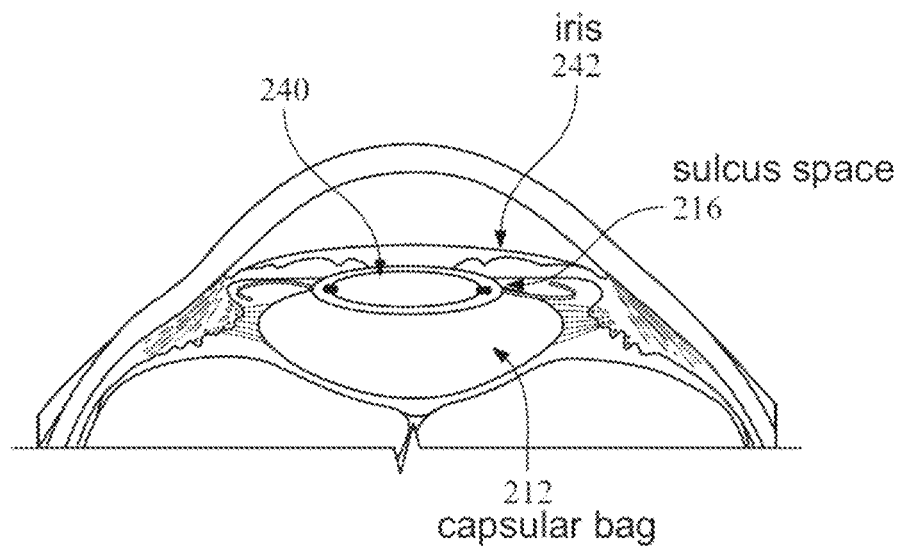
Figure 2E:
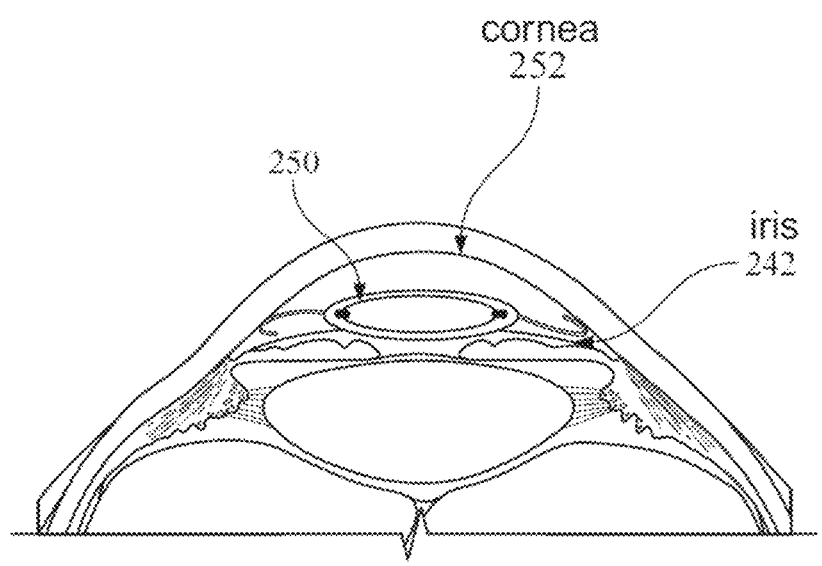

Referring to FIG. 2D, in some cases, an exchangeable optics system 240 can be positioned entirely in the sulcus 216 behind the iris 242, in front of the capsular bag 212. Referring to FIG. 2E, in some cases, an exchangeable optics system 250 can be positioned in the anterior chamber behind the cornea 252, in front of the iris 242. The examples shown in FIGS. 2D and 2E could work with a patient that is phakic (with native lens). Advantageously, if the intraocular base is fixed in the anterior chamber (such as shown in FIG. 2E) or in the sulcus space (such as shown in FIG. 2D), cataract surgery may not be required.

For any of these locations, if weight of the system is ever greater than zonular strength, an air bladder or portion of the device that floats in aqueous can be incorporated in the intraocular base. This buoyant component of the invention can be permanently incorporated, for example a compressible foam buoy that has sealed foam used in nautical equipment, pool toys and body boards. Alternatively, the device can have a reservoir that acts as a bladder that is filled with a gas or any material lighter than water. This would enable adjustable buoyancy based upon the degree of fill.

As mentioned above, the one or more couplers 110 (and corresponding one or more couplers 180) can include magnetic material or other releasable fixation material or structures. For example, the releasable couplers can be in the form of a hook and loop coupler, a memory material fixation element such as what is utilized for tagging guns for affixing tags to clothing, a button fastener, a screw-type fastener, a hinge-based fastener similar to a cuff link, a suction cup based mechanism, an adhesive, or any other means of reversible fixation.

Figures 3A, 3B:
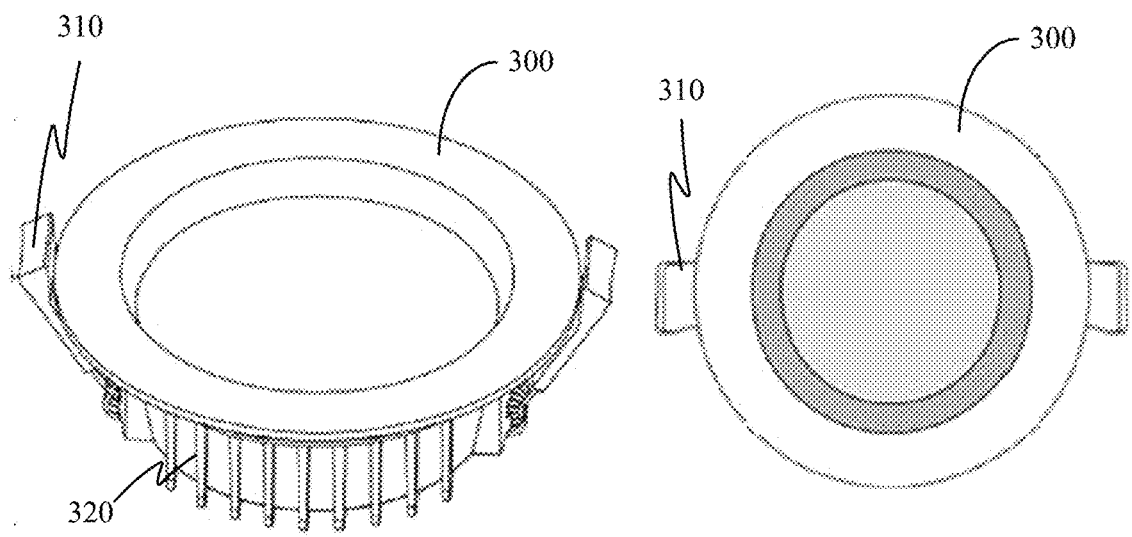
FIGS. 3A and 3B illustrate a perspective view and a top view, respectively, of an exchangeable optic with clips for coupling to an intraocular base.
Figure 4:
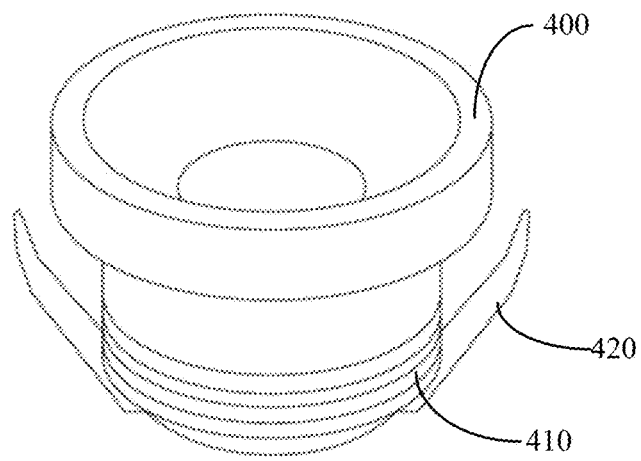
FIG. 4 illustrates a perspective view of an exchangeable optic with a screw mount for coupling to an intraocular base.

FIGS. 3A and 3B illustrate a perspective view and a top view, respectively, of an exchangeable optic with clips for coupling to an intraocular base; FIG. 4 illustrates a perspective view of an exchangeable optic with a screw mount for coupling to an intraocular base; and FIG. 5 illustrates a side view of part of an exchangeable optic system with a post and clip coupling.

Referring to FIGS. 3A and 3B, an exchangeable optic 300 can have a clip 310 that can attach to a coupler of an intraocular base (not shown). In some cases, the exchangeable optic 300 can include ribs 320 to assist with a secure fit, for example, within a main structure of the intraocular base.

Referring to FIG. 4, an exchangeable optic 400 can have a screw mount 410 for securing to a corresponding coupler at an intraocular base (not shown). In some cases, the exchangeable optic 400 can include prongs 420 to assist with a secure fit, for example, within a coupler and main structure of the intraocular base.

Figure 5:
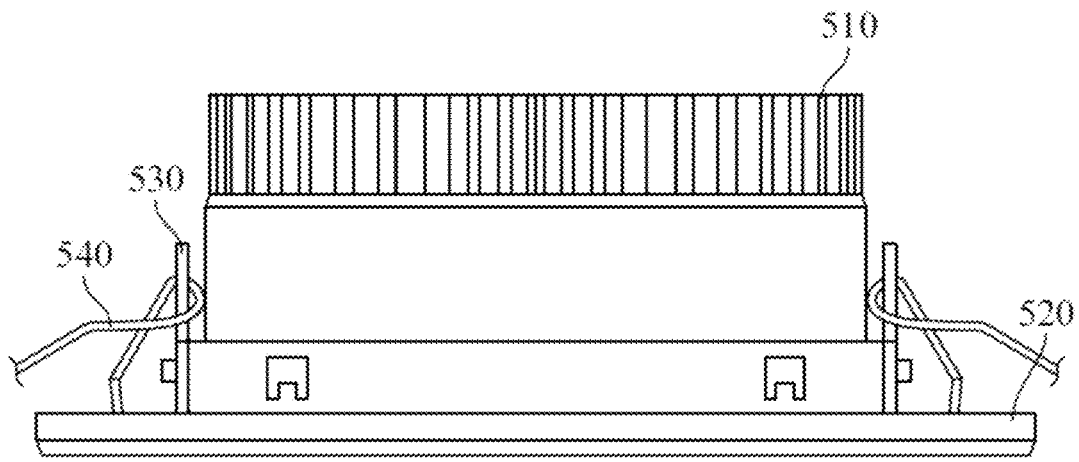
FIG. 5 illustrates a side view of part of an exchangeable optic system with a post and clip coupling.

Referring to FIG. 5, an exchangeable optic 510 can be coupled to an intraocular base 520 using a post 530 and nitinol clip 540.

For any direct connection between a base and an exchangeable optic (or between two exchangeable optics), it is desirable that the coupling mechanism is located within the confines of the anterior rhexis. This will enable direct connection between the exchangeable optic (e.g., exchangeable optic 225 of FIG. 2B) outside of the capsular bag 212 and the intraocular base (e.g., intraocular base 220 of FIG. 2B) in the capsular bag. Alternatively, femtosecond laser or other precision surgical platform can not only make the primary rhexis but also make two or more small secondary opening in the anterior capsule through which a coupling mechanism (e.g., extensions 222) can protrude. The use of the femtosecond laser or other precision surgical platform to form secondary openings through which a coupling mechanism can protrude may serve a secondary function of aligning a lens in a particular axis, which is useful, for example, with toric IOLs. Indeed, the femtosecond laser or other precision surgical platform can be used to make two additional holes adjacent to the rhexis at the axis the IOL must be through.

There are numerous coupling mechanisms that may be used instead of or in addition to magnetic material. In some cases, the exchangeable optic can have a fixation element that has a shape memory material component that can be placed through a hole at the intraocular base through the holes made in the anterior capsule. Similar to a tagging gun used to attach price tags to clothing, the T arms can flex when being pushed through the hole in the optic haptic junction and return to an open position once through the hole.

As is clear to one skilled in the art, this arrangement can be modified in numerous ways. For example, in some cases, the T arm fixation element can be incorporated into the intraocular base and project through the capsular bag into the sulcus space. The exchangeable optic can have a hole in it through which the T fixation element projects. This may be a preferable option if capsular bag phimosis causes the capsular bag to shift in position in relation to the hole in the primary optic. By having the T fixation element project beyond the capsular bag, this helps ensure maintained access to the coupling mechanism, even if capsular phimosis occurs. In addition, the T-shape fixation element can be made of a variety of memory materials including shape memory polymers and shape memory metals. Suitable memory polymers for the described fixation elements include, but are not limited to, polynorbomene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, and combinations thereof. Suitable memory metals for the described fixation elements include, but are not limited to, stainless steel, cobalt, nickel, chromium, molybdenum titanium, nitinol, tantalum, platinum-iridium alloy, gold, magnesium, or combinations thereof. Further, it should be understood that other end shapes may be used for the T shape fixation element. For example, the end shape may be a circle, triangle or any shape that is larger than the hole it is to be fixated through.

In some cases, the intraocular base or the exchangeable optic can have posts that project either through the anterior capsulotomy or through the secondary holes created in the anterior capsule. In one such implementation with a post projection, an exchangeable optic could then fit through the posts and an elastic band can be placed over the exchangeable optic onto the post thereby holding the exchangeable optic in place. The elastic band that retains the exchangeable optic can operate similar to how rubber bands hold a wire in place to the bracket on dental braces. In another implementation of a post projection, the post could have a thread on it in which a screw can mount. In another implementation, the post can include a hole through which a cotter pin or memory material can be placed through. In another implementation, the post can include a lever arm. Similar to a cuff link, the post can either be straight up and down or when turned at the hinge will form a T. This arrangement does not involve shape memory but instead just a mechanical hinge. An exchangeable optic with a feature similar to a shirt cuff can be threaded over the fixation element when it is in a straight position and then once in place the hinge can be turned so instead of straight the post forms a T thereby holding the exchangeable optic and the intraocular base together.

In some cases, the intraocular base and the exchangeable optic can use a snap-button arrangement, for example, if designed with low enough friction.

Figure 6A:
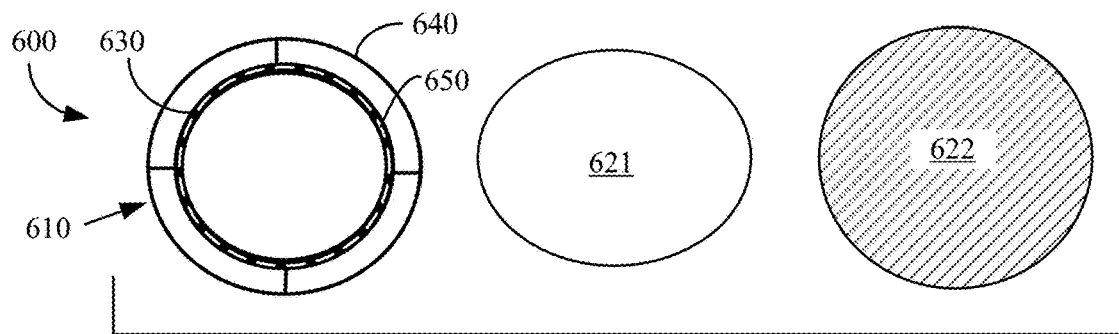
FIGS. 6A-6D illustrate an exchangeable optics system with multiple stacked lenses.
Figure 6B:
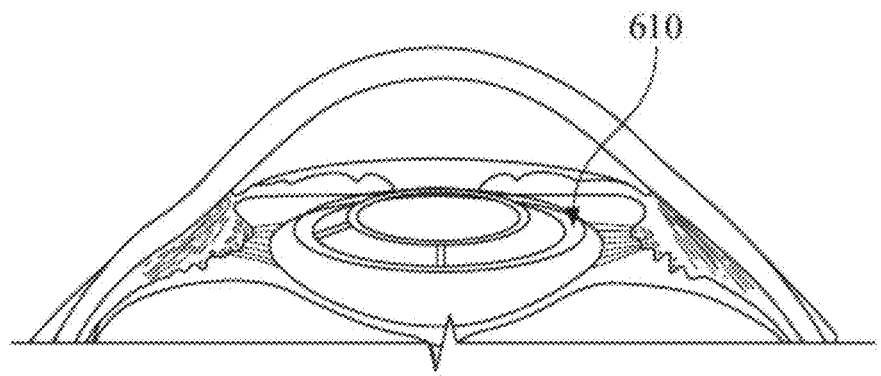
Figure 6C:
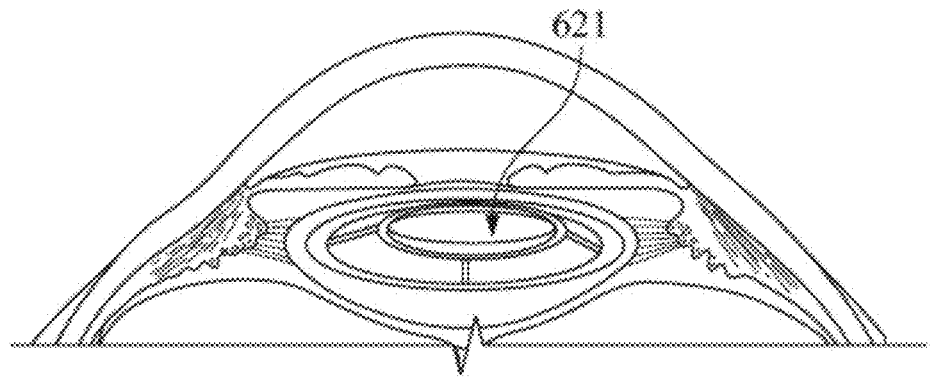
Figure 6D:
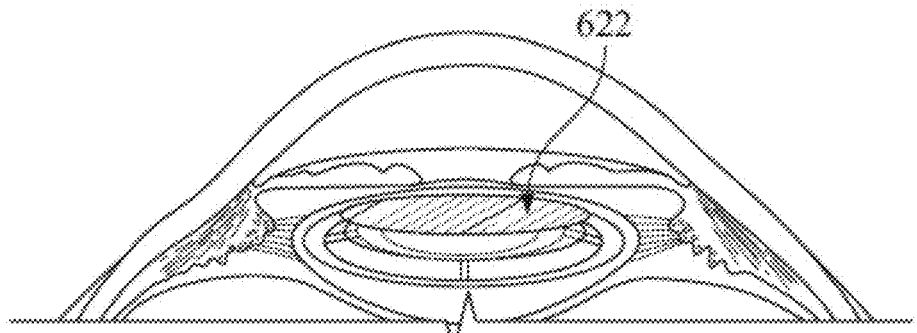

In some cases, the intraocular base and the exchangeable optic can use a twist on mechanism in conjunction with posts, where the posts include a T or L shaped end and once the posts pass through the opening in the other part, the exchangeable optic can be rotated so that the end of each post catches on a surface to hold the two in place. For example, if one post element is in the shape of a L but the slot it passes through only is slightly larger than the horizontal component of the L, then if the intraocular base and the exchangeable optic are rotated in relation to each other, the leading edge of the L moves beyond the edge of the slot it passes through thereby holding the intraocular based and the exchangeable optic together. In some cases, a shape memory material can be incorporated. For example, the L shape can have a projection at the very end (such as in the form of a very pronounced serif L). The projection at the end of the L can fit into a hole that is adjacent to the notch (e.g., similar to that employed in some ballpoint pens). Thus, as the L shape is threaded through the notch, the projection portion at the end of the L abuts the edge of the notch and is bent slightly out of the way so rotation can continue. Once rotated far enough that the projection on the L reaches the hole next to the notch and falls into place thereby enabling the L to again be coplanar with the intraocular base and exchangeable optic. In some cases, both the exchangeable optic and the L shaped post can be formed of materials with memory shape properties FIGS. 6A-6D illustrate an exchangeable optics system with multiple stacked lenses. FIG. 6A illustrates an exploded view of an exchangeable optics system 600 that includes an intraocular base 610 and a plurality of optics (including first optic 621 and second optic 622). The intraocular base 610 can have a supporting structure 630 with a haptic ring 640 that can be sutured for fixed connection to an eye. One or more couplers can be on the supporting structure. For example, the one or more couplers can be point sources or a ring (such as represented by white dotted line 650) that is disposed on or goes around a circumference of the supporting structure (see also e.g., FIGS. 11A and 11B). Referring to FIG. 6B, the intraocular base 610 can be disposed in the eye (e.g., in the sulcus space). As shown in FIG. 6C, the first optic 621 can be releasably attached to the intraocular base 610. Alternatively, in some cases, the first optic 621 (or a third optic) is fixedly attached to the intraocular base 610 or is built-in to the intraocular base (see e.g., lens 1060 of FIG. 10). Then, as shown in FIG. 6D, the second optic 622 can be releasably attached to the intraocular base 610 over the first optic 621. In some cases, the magnetic force from the intraocular base 610 is sufficient to couple both optics. In some cases, the positioning of the two optics enable at least a portion of the one or more couplers to be dedicated to a respective one of the two (or more) optics. In some cases, the first optic 621 includes one or more couplers for the second optic 622 to couple to. In some cases, the first optic 621 is fixedly attached to the intraocular base 610 and the couplers on the supporting structure are configured for attachment of the second optic 622.

Figure 7B:
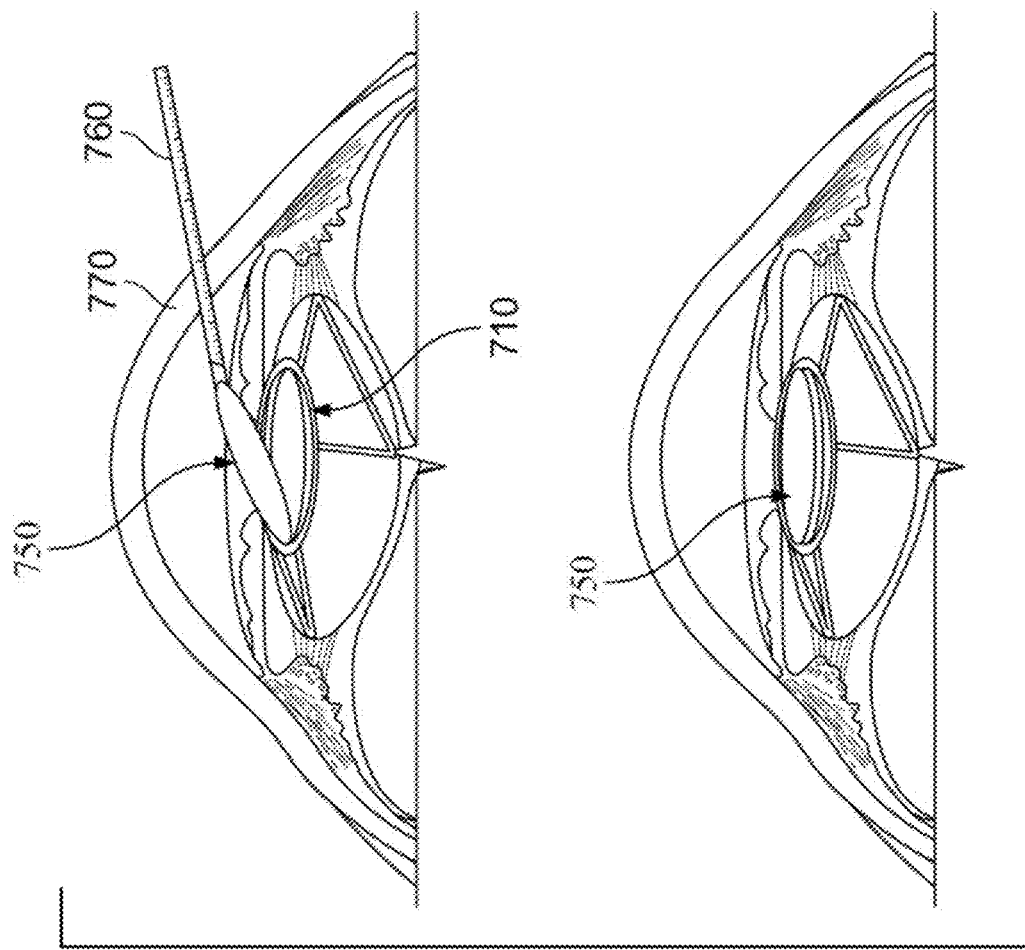
FIGS. 7A and 7B illustrate another exchangeable optics system with multiple stacked lenses.
Figure 7A:
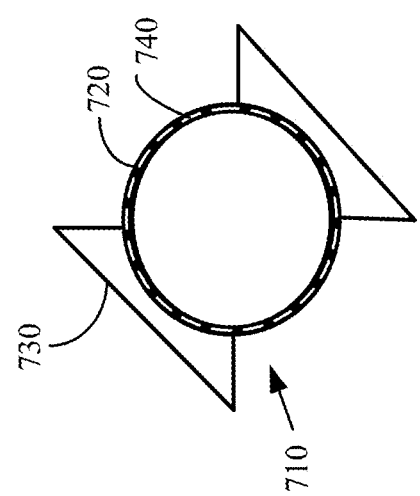

FIGS. 7A and 7B illustrate another exchangeable optics system with multiple stacked lenses; FIG. 7A shows another example of an intraocular base; and FIG. 7B shows application of a second optic onto the intraocular base and first optic using a delivery system.

Referring to FIG. 7A, an intraocular base 710 can have a supporting structure 720 with a haptic 730 that can be sutured for fixed connection to an eye. One or more couplers can be on the supporting structure 720. For example, the one or more couplers can be point sources or a ring (such as represented by white dotted line 740) that is disposed on or goes around a circumference of the supporting structure (see also e.g., FIGS. 11A and 11B).

Turning to FIG. 7B, a lens 750 can be easily applied to the intraocular base 710 via a tool (optic delivery system 760) through a small incision in the sclera 770. An optic delivery system 760 can include a hook or other fine instrument that can be drawn coaxially, allowing for a minimal incision that minimizes changes to corneal astigmatism and damage to the ocular structures after optic introduction or exchange. The optic delivery system can coaxially store a capsular bag containing a new optic containing, for example, the secondary lens 750 and enter through a minimal incision. As shown in FIG. 7B, once inside the eye close to the location of the intraocular base 710, the optic delivery system 760 can release the capsular bag close into the sulcus space. The hook (see FIG. 8) can be used to maneuver the capsular bag or secondary lens to be oriented properly with respect to the intraocular base 710. At some point, the new optic 750 can couple to the intraocular base, at which point the hook can optionally be used to properly orient the new optic with respect to the intraocular base. Fiducial markers may be used to facilitate orientation and alignment (see e.g., FIGS. 9A and 9B, which can be used under optical coherence tomography—OCT) In some cases, the exchangeable optics (e.g., lens 750) can include an aperture, which may be hooked by the instrument of the optic delivery system.

In this illustrated scenario, the lens 750 is a second optic; however, this method can be carried out for the first optic (e.g., optic 621) and even a replacement second optic (e.g., to replace the second optic 622 after optic 622 is applied as shown in FIG. 6D).

Figure 8:
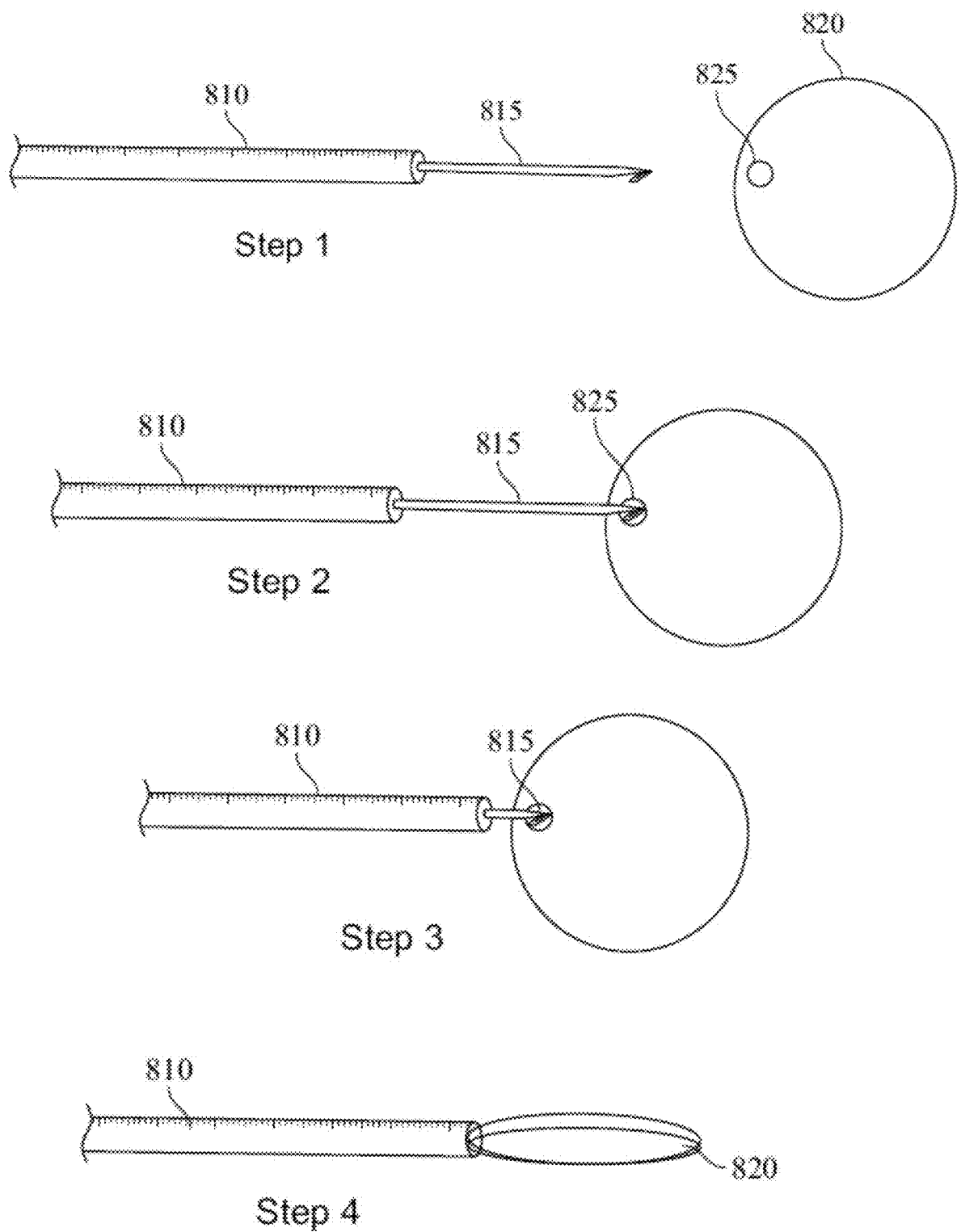
FIG. 8 illustrates an optic delivery system consisting of a hook that can be drawn coaxially within a delivery sleeve.

FIG. 8 illustrates operation of an optic delivery system. Referring to FIG. 8, an optic delivery system 810 can include a hook 815, which can be drawn coaxially into the eye within a delivery sleeve of the optic delivery system 810. In a first step, the hook 815 can be in the extended position. As illustrated in a second step, the hook 815 can engage a hole 825 within the periphery of the optic 820 to enable extraction. As illustrated in the third step, the hook 815 can then be drawn coaxially back into the optic delivery system 810, bringing the optic 820 towards the delivery sleeve. At a certain point, the hook 815 can be drawn entirely within the optic delivery system 810, at which point the optic 820 can be forced to fold inwards and be drawn with the hook into the optic delivery system 810, such as shown in step 4.

FIGS. 9A and 9B show fiducial designs that can enable precise orientation of three-dimensional rotation of an optic or haptic. Fiducials can be placed, etched, or drawn onto a lens or other optic to aid in orientation of the lens or other optic once deployed. The fiducial markers can be of a material suitable for detection by IR, ultrasound, fluorescent, x-ray, MRI, etc. In one implementation, the fiducials can be detectable by an ocular response analyzer (e.g., optical coherence tomography—OCT). The fiducial markers can be used to determine precise effective lens position (ELP). Corresponding markers can be applied to an intraocular base at haptics, on the optional lens, or on the supporting structure, as some examples. In some cases, a corresponding fiducial design may be disposed at the intraocular base (e.g., on main structure region 160 of FIG. 1A).

Referring to FIG. 9A, the fiducial can be L-shaped. Arms of the L shape can vary. If the size and shape of the L-shaped fiducial is known, apparent length can be used to inform rotation of the lens or optic in three dimensions. Referring to FIG. 9B, the fiducial can be bulls-eye-shaped (e.g., a single dot within a circle). In particular, use of a bulls-eye shape can allow part of the fiducial to be printed on an opposite side of the lens or optic. The fiducial being on both sides of the lens or optic can create greater apparent motion of the dot relative to the circle, allowing a more accurate understanding of its orientation in three-dimensional space.

A few L shaped fiducials printed on one side of the lens or haptic receiving system (e.g., as shown in FIG. 9A) or a circle on one side of the lens and a dot on the other placed within the circle when viewed anterior/posterior (e.g., providing a bullseye such as shown in FIG. 9B) will enable a sensitive measurement of any tilt. By visualizing the length of the L arms or where the dot is in relation to the circle it is possible to determine where the lens or haptic receiver is located.

In some implementations, fiducials are provided on both the exchangeable optic and the intraocular base that can be read using OCT. The fiducials can be read in relation to a stationary feature of the eye (e.g., conjunctival vessel pattern preregistered with corneal topography/tomography, biometry data, etc.). The OCT can then guide placement of the optic on haptic. The fiducials support real time tracking of the intraocular base in case the intraocular base moves when the exchangeable optic is removed. When the exchangeable optic is repositioned or replaced, the OCT device can calculate in real time with the fiducials what position change is necessary.

As mentioned above, an exchangeable optics system can include a variety of structures for the intraocular base. In addition, the couplers of the intraocular base can be disposed in various locations and be configured in various shapes. The following examples are directed to exchangeable optics systems with intraocular bases having magnetic coupling; however, embodiments are not limited thereto.

Figure 10:
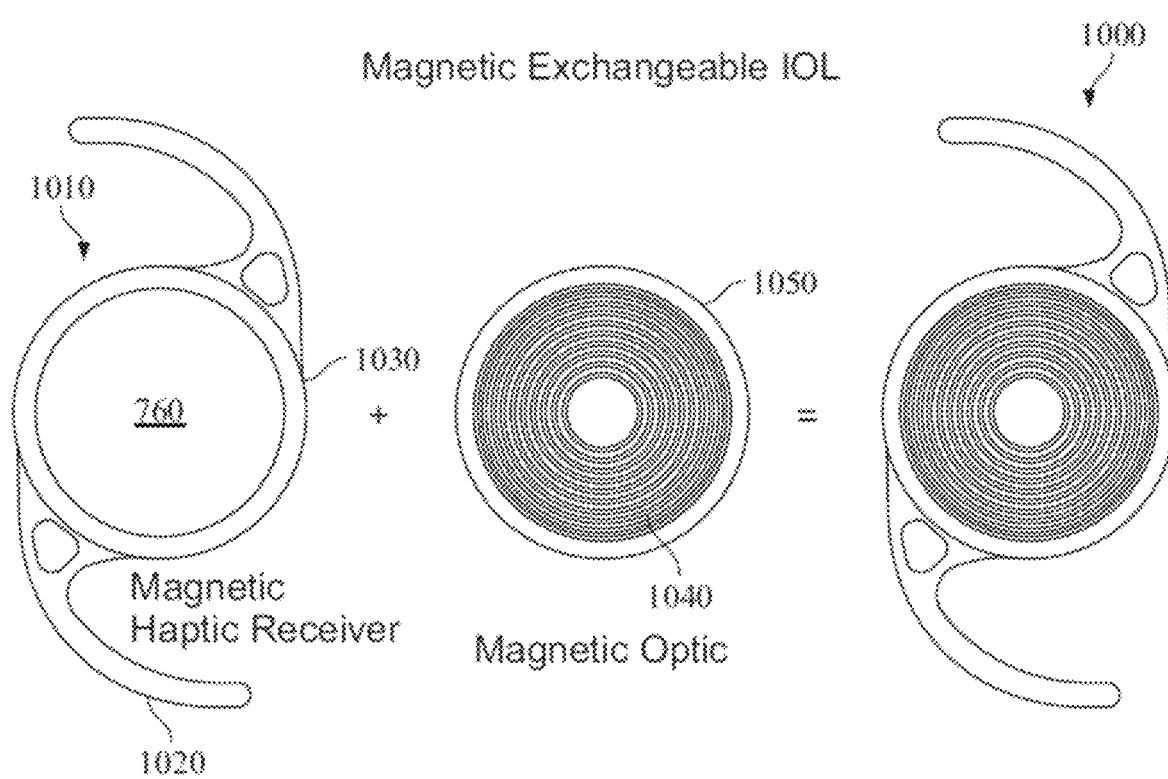
FIG. 10 illustrates an example exchangeable optics system with magnetic exchangeable intraocular lens.

FIG. 10 illustrates an example exchangeable optics system with magnetic exchangeable intraocular lens. Referring to FIG. 10, an exchangeable optics system 1000 can include an intraocular base 1010 with haptics 1020 and a circular magnet coupler 1030; and an exchangeable optic 1040. The exchangeable optic 1040 can be a magnetic optic with a corresponding circular magnet 1050 around its periphery.

In the illustrated scenario, the haptics 1020 are in the form of a two C-loop haptic. In some cases, the intraocular base 1010 can further include a lens 1060. For example, the intraocular base 1010 can be similar to a conventional IOL, but further includes the one or more couplers (e.g., here in the form of a magnet disposed at a periphery). A magnetic optic 1040 can then be deployed, rotated to any precise orientation, for example aligned using fiducials such as shown in FIGS. 9A and 9B, and coupled to the intraocular base structure 1010. In some cases, the exchangeable optic 1040 may not be deployed for potentially years down the line and/or may be replaced years later to deploy a more precise lens. An intraocular base structure 1010 that allows for deployment, rotation, and coupling of a magnetic optic (e.g., exchangeable optic 1040) can be advantageous, for example, in precise toric astigmatism correction. In addition, since it is possible to add additional lenses and/or replace the exchangeable optic 1040, it is possible to add a further corrective lens after a more disruptive surgery, add a corrective lens years after the fact, or deploy a more precise lens, for example a specially made or three-dimensional printed lens.

FIGS. 11A-11D illustrate another example of an exchangeable optics system with magnetic exchangeable ocular lens. Referring to FIGS. 11A and 11D, in exchangeable optics system 1100, an intraocular base 1110 can include a capsular tension ring 1120 with optional tension ring extensions 1125 and two or more couplers 1130. As mentioned above with respect to FIG. 2B, through use of one or more protrusions such as tensions ring extensions 1125, the capsular tension ring 1120 can be designed in such a way that two or more magnetic arms (e.g., tension ring extensions 1125 with couplers 1130) emerge through the anterior capsulotomy similar to an Ahmed segment thereby enabling optic placement in the sulcus space. Alternatively, the capsular tension ring can be designed such that the capsular tension ring does not rise up out of the anterior capsulotomy but instead remains in bag. In some cases, in addition to the couplers 1130 or as an alternative to the couplers 1130, a secondary magnet ring 1140 can be included, which can provide a 360-degree docking platform for magnetic optics 1150, as shown in FIGS. 11C and 11D. That is, as shown in FIG. 11C, an optic with corresponding couplers can be deployed, and attraction between the couplers 1130 on the arms of the capsular tension ring 1120 (and/or optionally the secondary magnet ring 1140) and the corresponding couplers on the optic 1150 can releasably maintain the optic 1150 in place.

Figure 12A:
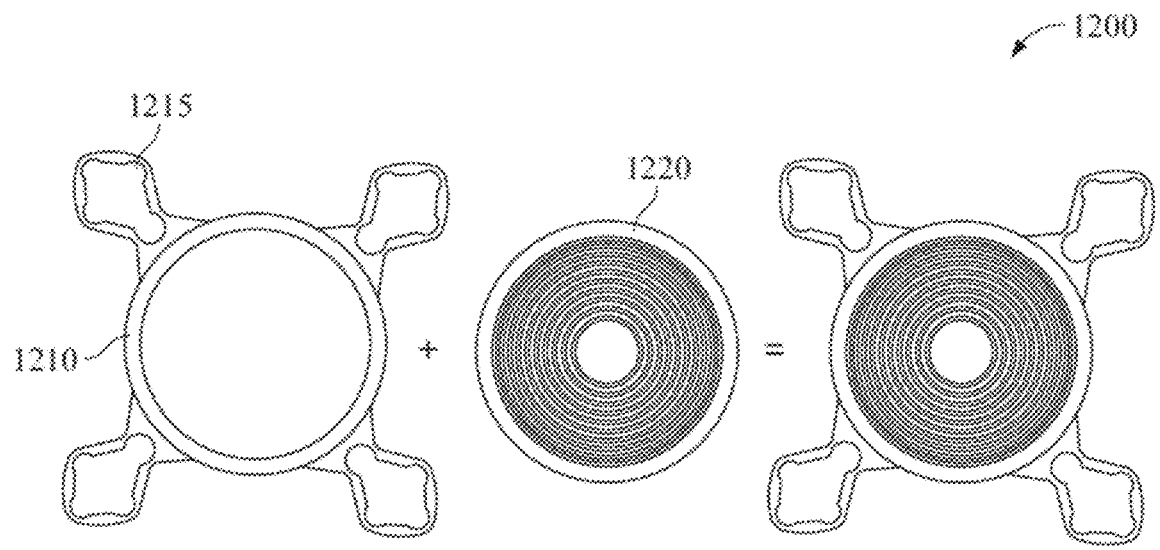
FIGS. 12A-12D illustrate example haptic designs for exchangeable optics systems.
Figure 12B:
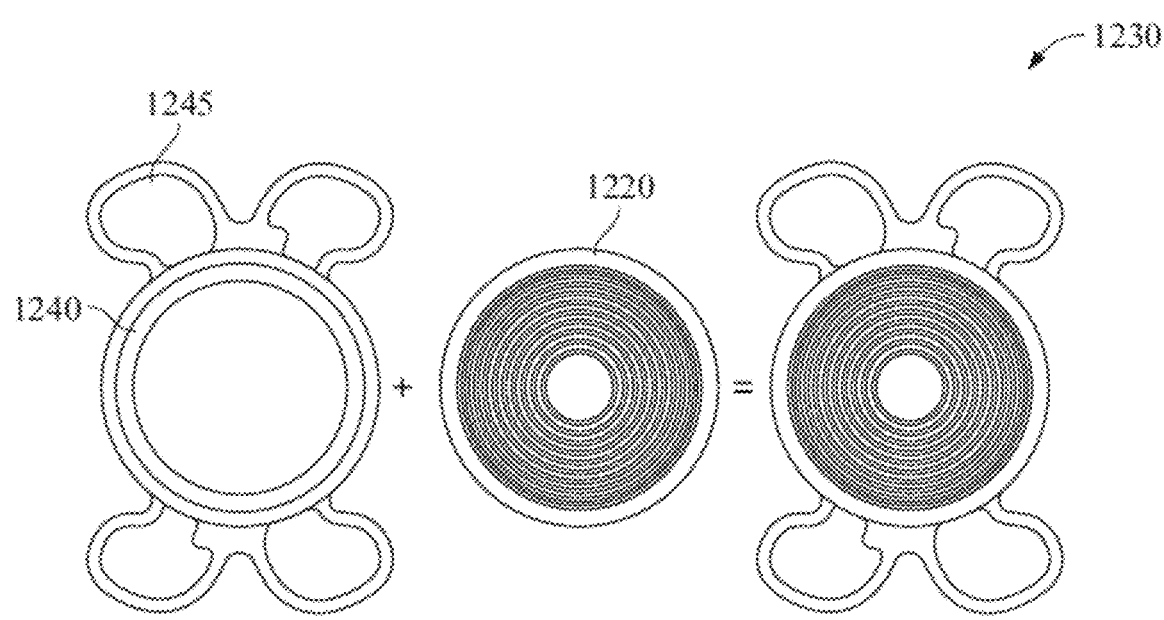
Figure 12C:
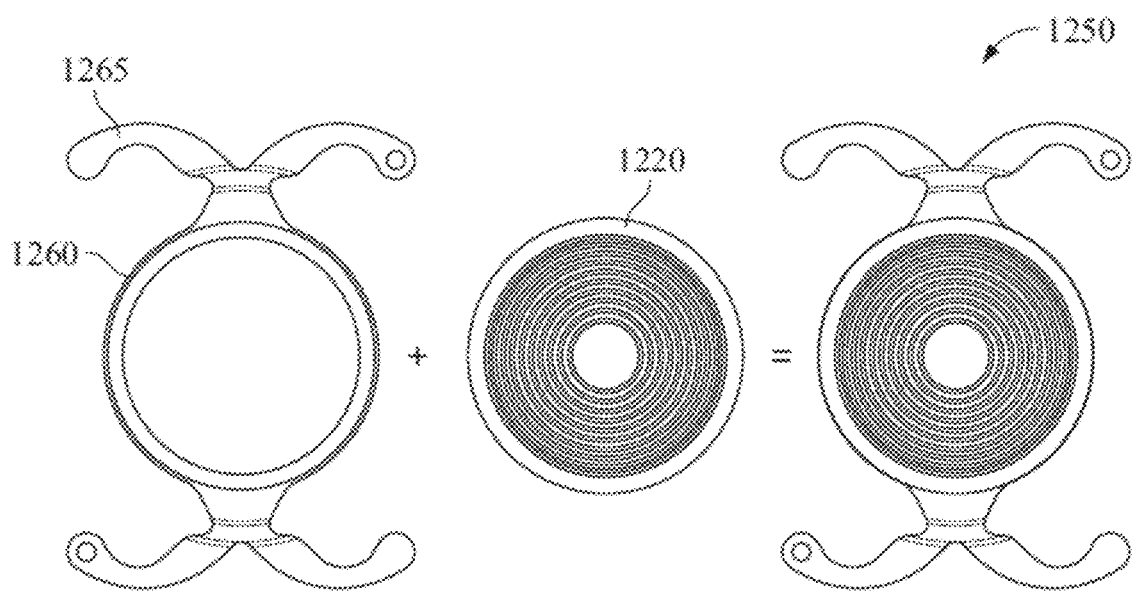
Figure 12D:
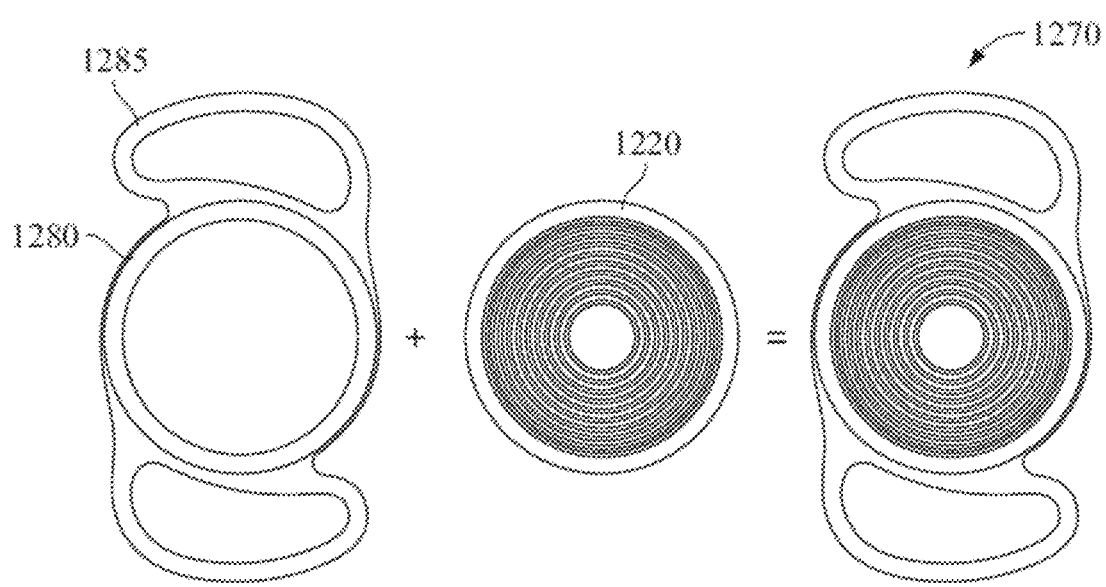

FIGS. 12A-12D illustrate example haptic designs for exchangeable optics systems. A supporting structure of an intraocular base can be implemented with haptics of a variety of different shapes and patterns. In addition to the shapes shown in FIGS. 6A and 7A, the two-looped C shaped haptic such as shown in FIG. 10 and the capsular tension ring configuration shown in FIG. 11A, other haptic shapes may be used. For example, FIG. 12A shows an exchangeable optics system 1200 with an intraocular base 1210 design having a cruciate haptic pattern 1215 and a magnetic coupling optic 1220. FIG. 12B shows an exchangeable optics system 1230 with an intraocular base 1240 design having a haptic design 1245 that can facilitate secondary scleral sutured lens similar to the Gore Akreos lens and a magnetic coupling optic 1220. FIG. 12C shows an exchangeable optics system 1250 with an intraocular base 1260 design with four-pronged haptic arm 1265 and a magnetic coupling optic 1220. FIG. 12D shows an exchangeable optics system 1270 with an intraocular base 1280 design with looped haptic 1285 and a magnetic coupling optic 1220.

With cataract surgery, the shape of the corneal as well as the optics of the lens and the effective lens position are altered. Even if precisely positioned in the appropriate location, postoperative shifting of the lens is not uncommon. An exchangeable optics system such as described herein can address these obstacles. First, by sandwiching the capsular bag between the magnetic optic and magnetic haptic receiver through the bag, the system is less likely to rotate or shift in relation to the capsular bag. Second, in certain embodiments, such as 3D printing of a wavefront guided custom intraocular lens, it may make more sense to allow an intraocular base with a lens haptic system to scar into the capsular bag. As the capsule contracts, the final effective lens position of the intraocular base will then be known. By including fiducials, a wavefront scan can calculate shape of cornea after cataract surgery, an effective lens position can be determined from fiducials, and this data can be used to 3D print a custom lens when all variables are achieved. The custom lens can then be attached afterwards to the determined specifications. This would enable the ability to not only print wavefront optimized monofocal IOLs, but also custom wavefront optimized multifocal and extended depth of focus intraocular lens. An intraocular base also provides a forward compatible system for any future iteration of lens since the lens can be replaced/exchanged with the newest iteration of the lens.

In some of such cases, the lens providing the primary power can be deployed with the intraocular base (see e.g., lens 1060 described with respect to FIG. 10) and a wavefront guided optic can be delivered secondarily for attachment to the intraocular base that has the lens 1060. The wavefront guided optic ("second lens") can be deployed through a far smaller incision and similar to ICL surgery and LASIK, may be amenable to office-based procedures. That is, the secondary optic can be deployed through a small enough corneal incision or previous surgical incisions can be accessed, and the additional variability created by reentering cornea can be minimized. This would enable the primary lens and haptic system to be deployed in the bag similar to current IOLs, just with a magnetic system. At a secondary time period in which the capsular bag has fully contracted, the fiducials provide effective lens position. In addition, by using topography/tomography and wavefront measurements of the length of the eye, all the optical variables could be controlled for. If necessary, the degree of astigmatism induced by penetrating the cornea to deliver the secondary optic can be controlled for with custom optic design adjusted to account for the induced astigmatism. Thus, it is possible to a priori determine effective lens position (ELP) and determine what custom or non-custom lens would be ideal for an eye.

Figure 13A:
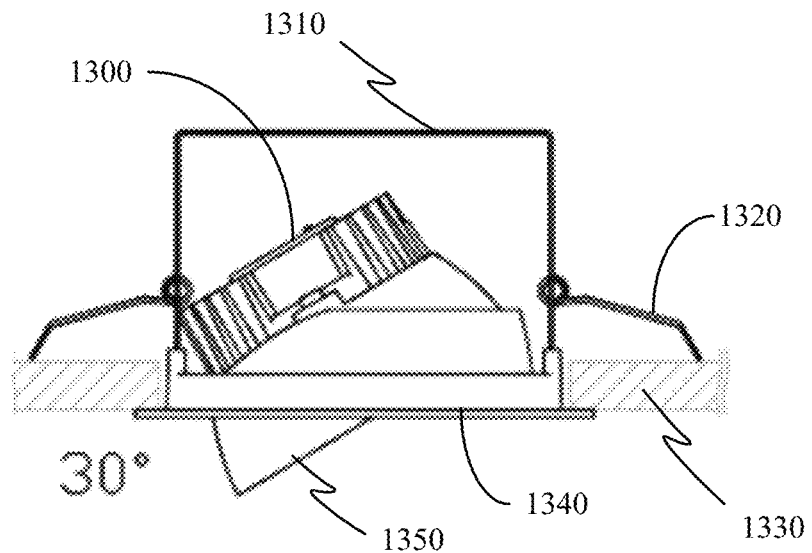
FIGS. 13A and 13B illustrate a side view and top view, respectively, of an exchangeable optic with rotatable lens.
Figure 13B:
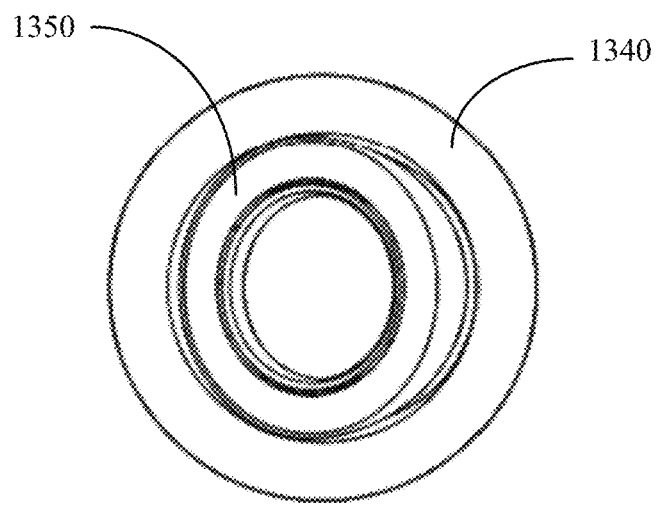

Specialized optics can be applied to an intraocular base as part of the described exchangeable optics systems. FIGS. 13A and 13B illustrate a side view and top view, respectively, of an exchangeable optic with rotatable lens. A lens housing system is provided for a rotational design that enables rotation of a lens of intraocular base or an exchangeable optic. Referring to FIG. 13A, a design for an exchangeable optic 1300 can have a coupling frame 1310 to which couplers 1320 of an intraocular base 1330 can be attached; a stationary body 1340 that can fit within an opening of the intraocular base 1330 and a rotating body 1350 which can rotate in one or two dimensions, depending on coupling between the stationary body 1340 and the rotating body 1350.

Figure 14A:
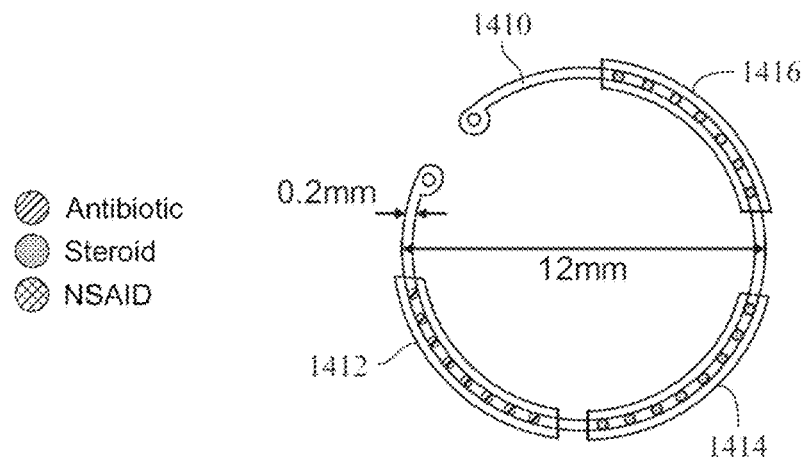
FIGS. 14A-14C illustrate an example of an exchangeable optics system with therapeutic delivery.
Figure 14B:
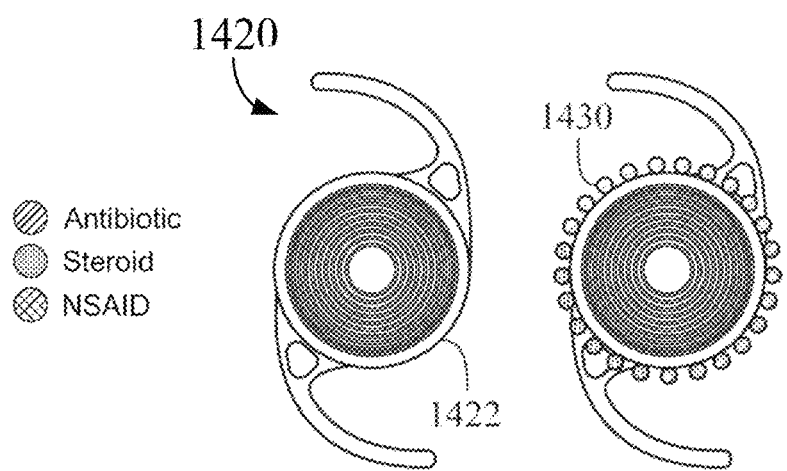
Figure 14C:
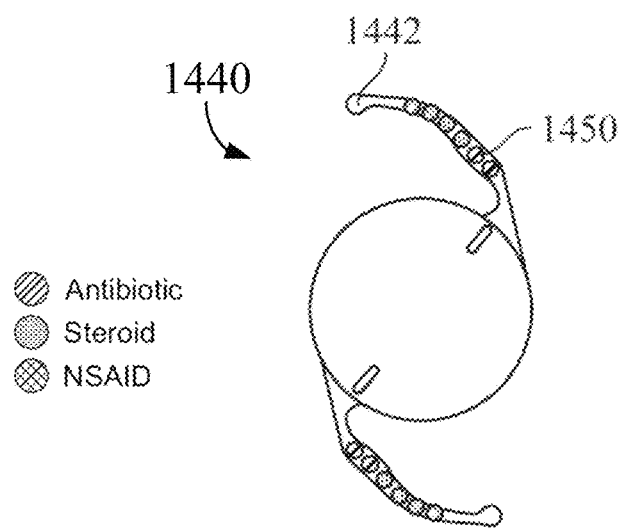

As previously mentioned, an intraocular base can be used not just to support delivery of exchangeable optics, but also to provide a surface for delivery of therapeutics. FIGS. 14A-14C an example of an exchangeable optics system with therapeutic delivery.

Magnetic liposomes or nanoparticles can be used in conjunction with magnetic components of an exchangeable optics system.

In addition to incorporating drug delivery polymeric implants or reservoirs directly into the haptic or optic system of the device, the magnetic components of the intraocular base provide a means of coupling magnetic nanoparticles and liposomes to the device. The magnetic liposomes or particles may be preloaded onto the device and administered at the time of surgery or after surgery.

Figure 15A:
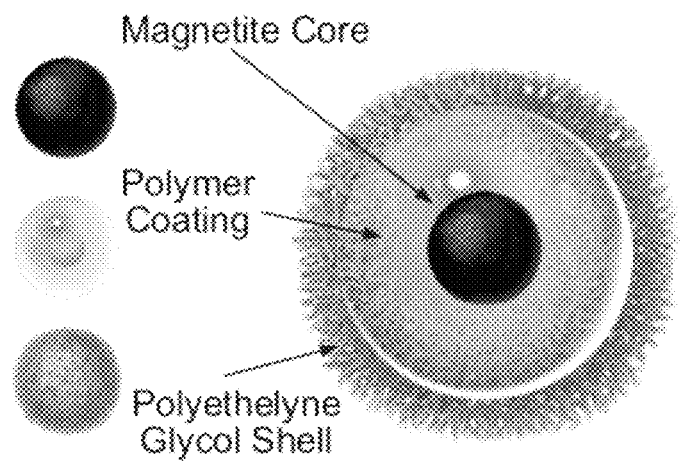
FIGS. 15A-15C illustrate example magnetic liposomes or nanoparticles that can be used for delivery of therapeutics on an exchangeable optics system.
Figure 15B:
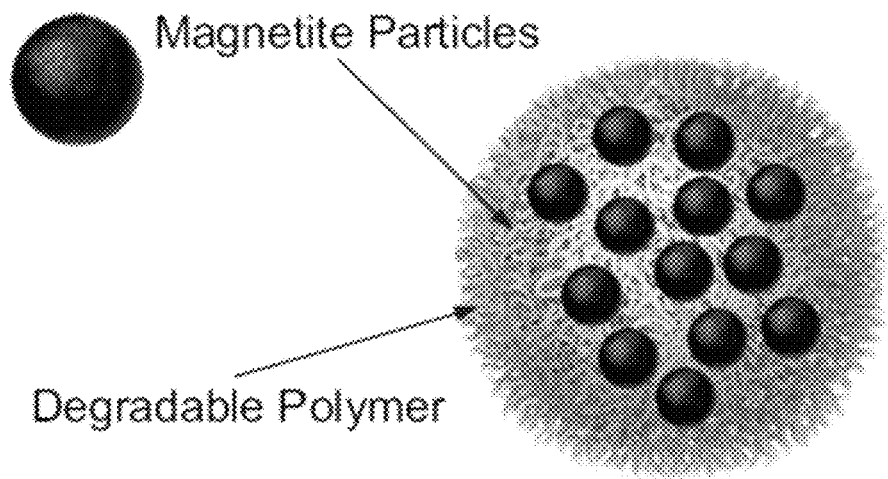
Figure 15C:
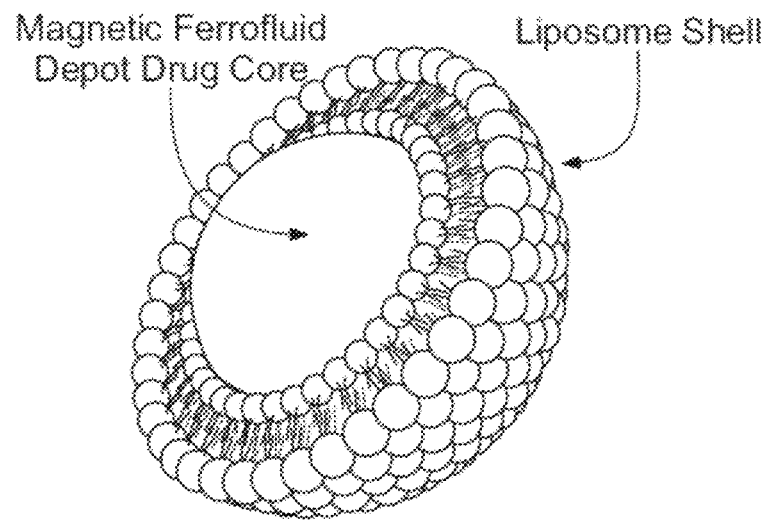

Magnetic liposomes or nanoparticles can be coupled to a magnetic intraocular base prior to deployment in the eye. Alternatively, or in addition, liposomes or nanoparticles can be introduced through an intravitreal, transzonular, intracapsular or intracameral approach after deployment of a magnetic intraocular base into the eye and be coupled to the magnetic intraocular base in the eye. The magnetic particles can be used to deliver therapeutics including, but not limited to antibiotics, steroids, and non-steroidal anti-inflammatory drugs (NSAIDs). These therapeutics can be configured such as illustrated in FIGS. 15A-15C to facilitate attachment to an intraocular base. Instead of rapidly exiting the eye through the normal outflow pathways, a magnetic intraocular base would enable the magnetic particles to dwell on the haptic system until they degraded or release ferrofluid to the point that the magnetic attraction is no longer sufficient to remain bound.

As mentioned above, the magnetic particles used to deliver the therapeutics can be applied to various forms of an intraocular base. Referring to FIG. 14A, an intraocular base 1410 in the form of a capsular tension ring can be formed of or coated with magnetic material that attracts the magnetic particles. In some cases, different regions can be applied with different therapeutics, for example, a region for antibiotics 1412, a region for steroid 1414, and a region for NSAID 1416. Of course, the therapeutics may be applied in a manner that the various therapeutics are disbursed throughout the surface of the intraocular base 1410.

Referring to FIG. 14B, an intraocular base 1420, with or without a lens, can include a magnetic coupler/ring 1422 that is used to attach magnetic particles 1430. The magnetic particles 1430 can thus be deployed and attached around the ring 1422.

Referring to FIG. 14C, an intraocular base 1440 with magnetic haptics 1442 can be used to attach magnetic particles 1450.

Referring to FIG. 15A, a magnetic particle can be formed of a magnetite core with polymer coating and polyethylene glycol shell. The magnetite cores can cause the magnetic particle to be attracted to the magnetic intraocular base allowing for relatively fine deployment. If a plurality of magnetite particles is present, attraction between the magnetic particle and the magnetic intraocular base is reduced. The strength of the magnet on the magnetic intraocular base as well as the concentration of the magnetite, size of polymer particle, and rate of degradation can adjust the dwell time to further finetune localized dosage. In a particular embodiment, rate of polymer degradation can be tuned to drug release rate. This can allow the magnetic particle to disassociate after the majority—or even all of—the drug is delivered due to a decreased attraction.

Referring to FIG. 15B, a magnetic particle can have a plurality of magnetic particles within a single polymer particle instead of a single magnetite core as shown in FIG. 15A.

Referring to FIG. 15C, a magnetic particle can be formed as a liposome particle with a ferrofluid core. A therapeutic can include a liposome shell, a magnetic ferrofluid within the liposome shell, and a drug or therapeutic core within the liposome shell. The magnetic ferrofluid and drug or therapeutic core can be combined inside the liposome shell. Since the ferrofluid and therapeutics are combined within the liposome shell, release of the drug or therapeutic can coincide with release of the ferrofluid. In certain implementations, rate of ferrofluid release can be tuned to drug release rate so when the majority of drug is released the degree of attraction between the liposome and intraocular base is reduced to the point at which the liposome dissociates and then can freely flow through the trabecular meshwork out of the eye.

Since free iron is known to be toxic to the retina, magnetic nanoparticles are contained within a biocompatible shell much like current iron-based MM contrast agents such as Ferridex® from Berlex Laboratories Inc. The nanoparticles are of sufficient size in order for them to freely egress out of the eye through the trabecular meshwork when the extraocular magnet is removed. The nanoparticles are then cleared by the liver like other iron-based nanoparticles currently used clinically.

The biocompatible material for the biocompatible shell of the magnetic nanoparticles can be selected from the group consisting of polyvinyl alcohol, sodium polyacrylate, acrylate polymers, hyaluronase polymers, collagen membrane, Porous HA/TCP ceramic composite, hydroxyapatite bone cement, PVP/PMMA, tricalcium phosphate, hydroxyapatite coated collagen fibers, calcium sulphate, hydroxyapatite (HAp), phosphorylcholine (PC), silicone, ultrahigh molecular weight polyethylene, polyethylene, acrylic, nylon, Polyurethane, Polypropylene, poly(methyl methacrylate), Teflon, Dacron, acetal, polyester, silicone-collagen composite, polyaldehyde, polyvinyl chloride), silicone-acrylate, poly(tetrafluoroethylene), hydroxyethyl methacrylate (HEMA), poly(methyl methacrylate) (PMMA), poly(glycolide lactide), poly(glycolic acid), tetrafluoroethylene, hexafluoropropylene, poly(glycolic acid), poly(lactic acid), desaminotyrosyltyrosine ethyl ester, polydioxanone, fibrin, gelatin, hyaluronan, tricalcium phosphate, polyglycolide (PGA), polycaprolactone, poly (lactide-co-glycolide), polyhydroxybutyrate, polyhydroxyvalerate, trimethylene carbonate, polyanhydrides, polyorthoesters, poly(vinyl alcohol), poly (N-vinyl 2-pyrrolidone), poly(ethylene glycol), poly(hydroxyethylmethacrylate), n-vinyl-2-pyrrolidone, methacrylic acid, methyl methacrylate, and maleic anhydride, polycaprolactone, poly(amino acids), poly(L-lysine), poly (l-ornithine), poly(glutamic acid), polycyanoacrylates, polyphosphazenes, poly(lactic acid), poly(glycolic acid), crown ethers, cyclodextrins, cyclophanes, ethylene glycol, Methylacrylate, Para-xylylene, Biodegradable Copolymers, Copolymer Surface Coatings, Starch Polymers, Polylactic Acid, Cellophane, Tyrosine Polycarbonates Lactide and Glycolide Polymers, Collagen, PTFE, silicone, Keratin-Based Materials, Fibrous Composites—Carbon Fiber and Particles, Polymer Composites, Artificial/Natural Material Composites, Glass-Ceramic/Metal Composites, Glass-Ceramic/Nonmetal Composites, Dental Composites, hydrogels, timed-release foams, and polymeric carriers.

According to certain implementations, the magnetic nanoparticles can include metal oxide and polymeric or liposomal formulations. Example liposomes include elements from the group consisting of fatty acids, fatty acids derivatives, mono-, di and triglycerides, phospholipids, sphingolipids, cholesterol and steroid derivatives, oils, vitamins and terpenes including but not limited to egg yolk L-phosphatidylcholine (EPC), 1,2-dimyristoyl-sn-glycero-3-phosphatidylcholine (DMPC), 1,2-dipalmitoyl-sn-glycero-3-phosphatidylcholine (DPPC), 1,2-dioleoyl-sn-glycero-3-phosphatidylcholine (DOPC), 1,2-distearoyl-sn-glycero-3-phosphatidylcholine (DSPC), 1,2-dilauroyl-sn-glycero-3-phosphatidylcholine (DLPC), 1,2-dioleoyl-sn-glycero-3-phosphaethanolamine (DOPE), 1-palmitoyl-oleoyl-sn-glycero-3-phosphoethanolamine (POPE), 1,2-dimyristoyl-sn-glycero-3-phosphoethanolamine (DMPE), 1,2-dipalmitoyl-sn-glycero-3-phosphoethanolamine (DPPE), and 1,2-distearoyl-sn-glycero-3-phospharthanolamine (DSPE), phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, 13-acyl-y-alkyl phospholipids, di-oleoyl phosphatidylcholine, di-myristoyl phosphatidylcholine, di-pentadecanoyl phosphatidylcholine, di-lauroyl phosphatidylcholine, dipalmitoylphosphatidylcholine, distearoylphosphatidylcholine, diarachidoylphosphatidylcholine, dibehenoylphosphatidylcholine, ditricosanoylphosphatidylcholine, dilignoceroylphatidylcholine; and phosphatidylethanolamines.

The polymer formulations (e.g., forming a matrix for the nanoparticles) can be selected from the group consisting of poly(acrylamide), poly(N-isopropylacrylamide), polyisopropylacrylamide-co-1-vinylimidazole), poly(N,N-dimethylacrylamide), poly(N,N-dimethylacrylamide), poly(1-vinylimidazole), poly(sodium acrylate), poly(sodium methacrylate), poly(2-hydroxyethylmethacrylate) (HEMA), poly N-dimethylaminoethyl methacrylate) (DMAEMA), poly(N tris(hydroxymethyl)methylacrylamide), poly(1-(3-methacryloxy)propylsulfonic acid) (sodium salt), poly(allylamine), poly(N-acryloxysuccinimide), poly(N-vinylcaprolactam), poly(1-vinyl-2-pyrrolidone), poly(2-acrylamido-2-methyl-1-propanesulfonic acid) (sodium salt), poly((3-acrylamidopropyl) trimethylammonium chloride), and poly(diallyldimethylammonium chloride), poly(hydroxy acids), polyanhydrides, polyorthoesters, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly (butyric acid), poly(valeric acid), and poly(lactide-co-caprolactone), ethylene vinyl acetate, copolymers and blends thereof.

Advantageously, the described intraocular base enables customization and exchange of optics as well as delivery of therapeutics.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. An exchangeable optics system comprising:
   an intraocular base comprising:
      one or more couplers for releasably coupling to an exchangeable optic or therapeutic; and
      a supporting structure for physically supporting the exchangeable optic or therapeutic when coupled to the intraocular base via the one or more couplers, the supporting structure comprising haptics for fixedly coupling the intraocular base within an eye, a main structure, and a first set of fiducials; and
   a therapeutic releasably coupled to the intraocular base,
   wherein the supporting structure comprises an intraocular lens (IOL), and wherein the main structure comprises a primary optic of the intraocular lens,
   wherein the one or more couplers are magnetic couplers located on a periphery of the main structure or on the haptics,
   wherein the therapeutic comprises a magnetic particle, and wherein the magnetic particle comprises:
      a liposome shell;
      a magnetic ferrofluid within the liposome shell; and
      a drug or therapeutic core within the liposome shell.

2. The exchangeable optics system of claim 1, further comprising:
   the exchangeable optic, wherein the exchangeable optic comprises one or more corresponding couplers for coupling with one or more magnetic couplers located on a periphery of the main structure.

3. The exchangeable optics system of claim 2, wherein the exchangeable optic comprises a wavefront guided optic and the primary optic provides base optical power.

4. The exchangeable optics system of claim 2, further comprising:
   a second set of fiducials on the exchangeable optic.

5. The exchangeable optics system of claim 1, wherein the one or more couplers comprises a magnetic ring on the main structure.

6. The exchangeable optics system of claim 1, wherein the one or more couplers releasably coupling the therapeutic to the intraocular base comprises magnetic material on a haptic of the supporting structure or a magnetic ring on the supporting structure.

* * * * *